(12) United States Patent
Hayashi

(10) Patent No.: US 8,742,176 B2
(45) Date of Patent: Jun. 3, 2014

(54) PROCESS FOR PRODUCING OPTICALLY ACTIVE 4-CHLORO-3-HYDROXYBUTANAL COMPOUND

(75) Inventor: Yujiro Hayashi, Sendai (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/880,640

(22) PCT Filed: Oct. 19, 2011

(86) PCT No.: PCT/JP2011/074072
§ 371 (c)(1),
(2), (4) Date: Apr. 19, 2013

(87) PCT Pub. No.: WO2012/053564
PCT Pub. Date: Apr. 26, 2012

(65) Prior Publication Data
US 2013/0217901 A1      Aug. 22, 2013

(30) Foreign Application Priority Data
Oct. 20, 2010   (JP) .................................. 2010-235792

(51) Int. Cl.
*C07C 47/02*   (2006.01)

(52) U.S. Cl.
USPC ........... 568/458; 568/420; 568/449; 548/400; 549/513

(58) Field of Classification Search
USPC ........... 568/420, 449, 458; 548/400; 549/200, 549/513
See application file for complete search history.

(56) References Cited

U.S. PATENT DOCUMENTS

2007/0196906 A1   8/2007   Matsumoto et al.

FOREIGN PATENT DOCUMENTS

| FR | 2 865 204 A | 7/2005 |
|---|---|---|
| JP | 2008-007457 A | 1/2008 |
| JP | 2010-013392 A | 1/2010 |
| WO | 2005/080299 A1 | 9/2005 |
| WO | 2005/098012 A1 | 10/2005 |

OTHER PUBLICATIONS

Barbas et al., *Journal of the American Chemical Society*, 112(5): 2013-2014 (1990).
Hayashi, *Journal of Synthetic Organic Chemistry, Japan*, 63 (5): 464-477 (2005) English abstract.
Hayashi et al., *Angewandte Chemie International Edition*, 50: 2804-2807 (2011).
Japanese Patent Office, International Search Report in International Patent Application No. PCT/JP2011/074072 (Dec. 13, 2011) English translation.
Markert et al., *Journal of the American Chemical Society*, 131(46): 16642-16643 (2009).
European Patent Office, Extended European Search Report in European Patent Application No. 11834403.5 (Feb. 24, 2014).

*Primary Examiner* — Golam M M Shameem
(74) *Attorney, Agent, or Firm* — Leydig, Voit & Mayer, Ltd.

(57) ABSTRACT

The invention relates to a method of producing optically active 4-chloro-3-hydroxybutanal compound (2) by reacting chloroacetaldehyde with aldehyde compound (1) in the presence of optically active pyrrolidine compound (5).

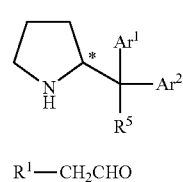

(5)

$R^1$—$CH_2CHO$ (1)

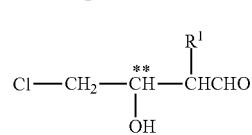

(2)

wherein each symbol is as defined in the specification.

10 Claims, No Drawings

PROCESS FOR PRODUCING OPTICALLY ACTIVE 4-CHLORO-3-HYDROXYBUTANAL COMPOUND

CROSS-REFERENCE TO RELATED APPLICATIONS

This patent application is the U.S. national phase of International Patent Application No. PCT/JP2011/074072, filed on Oct. 19, 2011, which claims the benefit of Japanese Patent Application No. 2010-235792, filed Oct. 20, 2010, which are incorporated by reference in their entireties herein.

TECHNICAL FIELD

The present invention relates to a production method of a 4-chloro-3-hydroxybutanal compound.

BACKGROUND ART

An optically active compound represented by the formula (2)

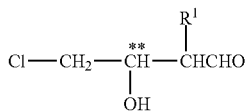

wherein each symbol is as defined below, is known to be useful as an intermediate for producing a medicament, a pesticide and the like, since it can be converted to, for example, an optically active hexahydrofurofuranol derivative.

Concerning a production method of an optically active compound represented by the formula (2), non-patent document 1 discloses that an optically active 4-chloro-3-hydroxy-2-methylbutanal can be obtained, for example, by reacting chloroacetaldehyde with propanal in the presence of an enzyme.

DOCUMENT LIST

Non-Patent Document

Non-Patent Document 1: Journal of the American Chemical Society, vol. 112, pages 2013-2014, 1990

SUMMARY OF THE INVENTION

Problems to be Solved by the Invention

The aim of the present invention is to provide a new method capable of producing an optically active compound represented by the formula (2) without using an enzyme.

Means of Solving the Problems

Under the circumstances, the present inventors have studied a new production method of an optically active compound represented by the formula (2) without using an enzyme, and found that a reaction in the presence of a particular asymmetric catalyst is superior in the production of an optically active compound represented by the formula (2), which resulted in the completion of the present invention. Accordingly, the present invention is as follows.

[1] A method of producing an optically active compound represented by the formula (2):

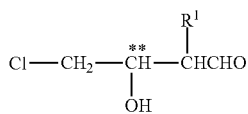

wherein
$R^1$ is a $C_1$-$C_{20}$ hydrocarbon group optionally having substituent(s) selected from the following Group G1 or a hydrogen atom, and
the carbon atom marked with ** is an asymmetric carbon atom (hereinafter referred to as optically active 4-chloro-3-hydroxybutanal compound (2)),
which comprises a step of reacting chloroacetaldehyde with a compound represented by the formula (1):

$$R^1\text{—}CH_2CHO \qquad (1)$$

wherein
$R^1$ is as defined above
(hereinafter referred to as aldehyde compound (1)), in the presence of an optically active compound represented by the formula (5):

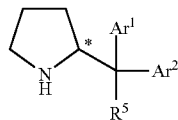

wherein
$Ar^1$ and $Ar^2$ are each independently a phenyl group optionally having substituent(s) selected from the following Group G2, a $C_1$-$C_{12}$ chain hydrocarbon group, a $C_3$-$C_{12}$ alicyclic hydrocarbon group or a hydrogen atom,
$R^5$ is a hydrogen atom, a fluorine atom, a hydroxyl group, a $C_1$-$C_{12}$ alkoxy group, a $C_1$-$C_{12}$ fluorinated alkyloxy group or a group represented by —$OSiR^6R^7R^8$ wherein $R^6$, $R^7$ and $R^8$ are each independently a $C_1$-$C_8$ alkyl group or a $C_6$-$C_{20}$ aryl group, and the carbon atom marked with * is an asymmetric carbon atom (hereinafter referred to as pyrrolidine compound (5));
<Group G1>: a group consisting of a $C_6$-$C_{20}$ aryl group optionally having substituent(s) selected from Group G2, an aromatic heterocyclic group optionally having substituent(s) selected from Group G2, a $C_1$-$C_{12}$ alkoxy group, a $C_1$-$C_{12}$ alkoxy group having $C_6$-$C_{20}$ aryl group(s) optionally having substituent(s) selected from Group G2, a halogen atom, an oxo group and a tri-$C_1$-$C_{12}$ alkylsilyl group;
<Group G2>: a group consisting of a $C_1$-$C_{12}$ alkyl group, a $C_1$-$C_{12}$ alkoxy group, a $C_2$-$C_{13}$ alkoxycarbonyl group, a $C_1$-$C_{12}$ fluorinated alkyl group, a $C_2$-$C_{13}$ acyl group, a nitro group, a cyano group, a protected amino group and a halogen atom.
[2] The method of the above-mentioned [1], wherein the reaction is carried out in a solvent containing an organic solvent.
[3] The method of the above-mentioned [1], wherein $R^1$ is not a hydrogen atom, and the reaction is carried out in a mixed solvent of water and an organic solvent selected from an alcohol solvent, an ether solvent, a nitrile solvent and an aprotic polar solvent.

[4] The method of any of the above-mentioned [1]-[3], wherein $R^5$ is a hydroxyl group.

[5] The method of any of the above-mentioned [1]-[4], wherein $R^5$ is a hydroxyl group, and $Ar^1$ and $Ar^2$ are each independently a phenyl group optionally having $C_1$-$C_{12}$ fluorinated alkyl group(s).

[6] The method of any of the above-mentioned [1]-[4], wherein $R^5$ is a hydroxyl group, and $Ar^1$ and $Ar^2$ are both 3,5-bis(trifluoromethyl)phenyl groups.

[7] A method of producing an optically active compound represented by the formula (3):

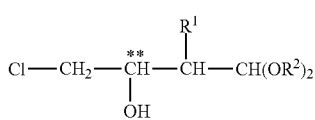

(3)

wherein
$R^1$ and ** are as defined in the above-mentioned [1], and
$R^2$ is a $C_1$-$C_{10}$ alkyl group, and two of $R^2$ in combination form a $C_2$-$C_{10}$ alkanediyl group optionally having substituent(s) selected from the following Group G1
(hereinafter referred to as optically active acetal compound (3)), which comprises
a step of producing optically active 4-chloro-3-hydroxybutanal compound (2) according to the method of any of the above-mentioned [1]-[6]; and
a step of subjecting optically active 4-chloro-3-hydroxybutanal compound (2) obtained the above-mentioned step to acetalization;
<Group G1>: a group consisting of a $C_6$-$C_{20}$ aryl group optionally having substituent(s) selected from Group G2, an aromatic heterocyclic group optionally having substituent(s) selected from Group G2, a $C_1$-$C_{12}$ alkoxy group, a $C_1$-$C_{12}$ alkoxy group having $C_6$-$C_{20}$ aryl group(s) optionally having substituent(s) selected from Group G2, a halogen atom, an oxo group and a tri-$C_1$-$C_{12}$ alkylsilyl group;
<Group G2>: a group consisting of a $C_1$-$C_{12}$ alkyl group, a $C_1$-$C_{12}$ alkoxy group, a $C_6$-$C_{20}$ alkoxycarbonyl group, a $C_1$-$C_{12}$ fluorinated alkyl group, a $C_2$-$C_{13}$ acyl group, a nitro group, a cyano group, a protected amino group and a halogen atom.

[8] A method of producing an optically active compound represented by the formula (6):

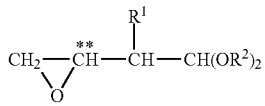

(6)

wherein
$R^1$ and ** are as defined in the above-mentioned [1], and
$R^2$ is as defined in the above-mentioned [7] (hereinafter referred to as optically active epoxy compound (6)), which comprises
a step of producing optically active 4-chloro-3-hydroxybutanal compound (2) according to the method of any of the above-mentioned [1]-[6];
a step of subjecting optically active 4-chloro-3-hydroxybutanal compound (2) obtained the above-mentioned step to acetalization; and a step of reacting optically active acetal compound (3) obtained the above-mentioned step with a base;
<Group G1>: a group consisting of a $C_6$-$C_{20}$ aryl group optionally having substituent(s) selected from Group G2, an aromatic heterocyclic group optionally having substituent(s) selected from Group G2, a $C_1$-$C_{12}$ alkoxy group, a $C_1$-$C_{12}$ alkoxy group having $C_6$-$C_{20}$ aryl group(s) optionally having substituent(s) selected from Group G2, a halogen atom, an oxo group and a tri-$C_1$-$C_{12}$ alkylsilyl group;
<Group G2>: a group consisting of a $C_1$-$C_{12}$ alkyl group, a $C_1$-$C_{12}$ alkoxy group, a $C_2$-$C_{13}$ alkoxycarbonyl group, a $C_1$-$C_{12}$ fluorinated alkyl group, a $C_2$-$C_{13}$ acyl group, a nitro group, a cyano group, a protected amino group and a halogen atom.

[9] A method of producing an optically active compound represented by the formula (4):

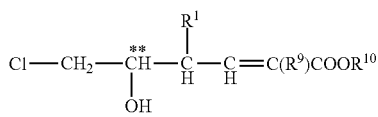

(4)

wherein
$R^1$ and ** are as defined in the above-mentioned [1],
$R^9$ is a hydrogen atom or a $C_1$-$C_8$ alkyl group, and
$R^{10}$ is a $C_1$-$C_8$ alkyl group
(hereinafter referred to as optically active α,β-unsaturated ester compound (4)), which comprises
a step of producing optically active 4-chloro-3-hydroxybutanal compound (2) according to the method of any of the above-mentioned [1]-[6]; and
a step of reacting optically active 4-chloro-3-hydroxybutanal compound (2) obtained the above-mentioned step with $Ph_3P=C(R^9)CO_2R^{10}$ wherein Ph is a phenyl group, and $R^9$ and $R^{10}$ are as defined above.

[10] A method of producing an optically active compound represented by the formula (7):

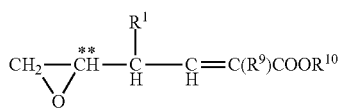

(7)

wherein
$R^1$ and ** are as defined in the above-mentioned [1], and
$R^9$ is a hydrogen atom or a $C_1$-$C_8$ alkyl group, and
$R^{10}$ is a $C_1$-$C_8$ alkyl group
(hereinafter referred to as optically active epoxy compound (7)), which comprises
a step of producing optically active 4-chloro-3-hydroxybutanal compound (2) according to the method of any of the above-mentioned [1]-[6];
a step of reacting optically active 4-chloro-3-hydroxybutanal compound (2) obtained the above-mentioned step with $Ph_3P=C(R^9)CO_2R^{10}$ wherein Ph is a phenyl group, and $R^9$ and $R^{10}$ are as defined above; and
a step of reacting optically active α,β-unsaturated ester compound (4) obtained the above-mentioned step with a base.

Effect of the Invention

The production method of the present invention can provide a new method capable of producing optically active 4-chloro-3-hydroxybutanal compound (2).

DESCRIPTION OF EMBODIMENTS

The present invention is explained in detail below.

In the present specification, the "halogen atom" means a fluorine atom, a chlorine atom, a bromine atom or an iodine atom.

In the present specification, the "$C_1$-$C_{20}$ hydrocarbon group" means a $C_1$-$C_{20}$ aliphatic hydrocarbon group or a $C_6$-$C_{20}$ aromatic hydrocarbon group.

In the present specification, the "$C_1$-$C_{20}$ aliphatic hydrocarbon group" means a $C_1$-$C_{20}$ chain hydrocarbon group or a $C_3$-$C_{20}$ alicyclic hydrocarbon group.

In the present specification, the "$C_1$-$C_{12}$ aliphatic hydrocarbon group" means a $C_1$-$C_{12}$ chain hydrocarbon group or a $C_3$-$C_{12}$ alicyclic hydrocarbon group.

In the present specification, the "$C_1$-$C_{20}$ chain hydrocarbon group" means a $C_1$-$C_{20}$ alkyl group, a $C_2$-$C_{20}$ alkenyl group or a $C_2$-$C_{20}$ alkynyl group.

In the present specification, the "$C_1$-$C_{12}$ chain hydrocarbon group" means a $C_1$-$C_{12}$ alkyl group, a $C_2$-$C_{12}$ alkenyl group or a $C_2$-$C_{12}$ alkynyl group.

In the present specification, the "$C_1$-$C_{20}$ alkyl group" means a straight or branched chain alkyl group having 1 to 20 carbon atoms, and examples thereof include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl, undecyl, dodecyl, tridecyl, eicosyl and the like. Among them, a $C_1$-$C_{12}$ alkyl group is preferable, and a $C_1$-$C_8$ alkyl group is particularly preferable.

In the present specification, the "$C_1$-$C_{12}$ alkyl group" means a straight or branched chain alkyl group having 1 to 12 carbon atoms, and examples thereof include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl, undecyl, dodecyl and the like. Among them, a $C_1$-$C_8$ alkyl group is preferable, and a $C_1$-$C_4$ alkyl group is particularly preferable.

In the present specification, the "$C_1$-$C_8$ alkyl group" means a straight or branched chain alkyl group having 1 to 8 carbon atoms, and examples thereof include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl and the like. Among them, a $C_1$-$C_4$ alkyl group is preferable.

In the present specification, the "$C_1$-$C_6$ alkyl group" means a straight or branched chain alkyl group having 1 to 6 carbon atoms, and examples thereof include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl and the like. Among them, a $C_1$-$C_4$ alkyl group is preferable.

In the present specification, the "$C_1$-$C_4$ alkyl group" means a straight or branched chain alkyl group having 1 to 4 carbon atoms, and examples thereof include methyl, ethyl, propyl, isopropyl, butyl, isobutyl, sec-butyl, tert-butyl and the like.

In the present specification, the "$C_2$-$C_{20}$ alkenyl group" means a straight or branched chain alkenyl group having 2 to 20 carbon atoms, and examples thereof include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl, 1-nonenyl, 1-decenyl, 1-undecenyl, 1-dodecenyl, 1-tridecenyl, 1-eicosenyl and the like. Among them, a $C_2$-$C_{12}$ alkenyl group is preferable, and a $C_2$-$C_8$ alkenyl group is particularly preferable.

In the present specification, the "$C_2$-$C_{12}$ alkenyl group" means a straight or branched chain alkenyl group having 2 to 12 carbon atoms, and examples thereof include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl, 1-nonenyl, 1-decenyl, 1-undecenyl, 1-dodecenyl and the like. Among them, a $C_2$-$C_8$ alkenyl group is preferable, and a $C_2$-$C_4$ alkenyl group is particularly preferable.

In the present specification, the "$C_2$-$C_6$ alkenyl group" means a straight or branched chain alkenyl group having 2 to 6 carbon atoms, and examples thereof include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl and the like. Among them, a $C_2$-$C_4$ alkenyl group is particularly preferable.

In the present specification, the "$C_2$-$C_{20}$ alkynyl group" means a straight or branched chain alkynyl group having 2 to 20 carbon atoms, and examples thereof include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl, 1-nonynyl, 1-decynyl, 1-undecynyl, 1-dodecynyl, 1-tridecynyl, 1-eicosynyl and the like. Among them, a $C_2$-$C_{12}$ alkynyl group is preferable, and a $C_2$-$C_8$ alkynyl group is particularly preferable.

In the present specification, the "$C_2$-$C_{12}$ alkynyl group" means a straight or branched chain alkynyl group having 2 to 12 carbon atoms, and examples thereof include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl, 1-nonynyl, 1-decynyl, 1-undecynyl, 1-dodecynyl and the like. Among them, a $C_2$-$C_8$ alkynyl group is preferable, and a $C_2$-$C_4$ alkynyl group is particularly preferable.

In the present specification, the "$C_2$-$C_6$ alkynyl group" means a straight or branched chain alkynyl group having 2 to 6 carbon atoms, and examples thereof include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. Among them, a $C_2$-$C_4$ alkynyl group is preferable.

In the present specification, the "$C_3$-$C_{20}$ alicyclic hydrocarbon group" means a $C_3$-$C_{20}$ cycloalkyl group or a $C_4$-$C_{20}$ cycloalkenyl group.

In the present specification, the "$C_3$-$C_{12}$ alicyclic hydrocarbon group" means a $C_3$-$C_{12}$ cycloalkyl group or a $C_4$-$C_{12}$ cycloalkenyl group.

In the present specification, the "$C_3$-$C_{20}$ cycloalkyl group" means a cyclic alkyl group having 3 to 20 carbon atoms, and examples thereof include cyclopropyl, cyclobutyl, cyclopentyl, cyclohexyl, cycloheptyl, cyclooctyl, cyclononyl, cyclodecyl, cycloundecyl, cyclododecyl, cyclotridecyl, cycloeicosyl and the like. Among them, a $C_3$-$C_{12}$ cycloalkyl group is preferable, and a $C_3$-$C_8$ cycloalkyl group is particularly preferable.

In the present specification, the "$C_3$-$C_{12}$ cycloalkyl group" means a cyclic alkyl group having 3 to 12 carbon atoms, and examples thereof include cyclopropyl, cyclobutyl, cyclopentyl, cyclohexyl, cycloheptyl, cyclooctyl, cyclononyl, cyclodecyl, cycloundecyl, cyclododecyl and the like. Among them, a $C_3$-$C_8$ cycloalkyl group is preferable.

In the present specification, the "$C_4$-$C_{20}$ cycloalkenyl group" means a cyclic alkenyl group having 4 to 20 carbon atoms, and examples thereof include 2-cyclopenten-1-yl, 3-cyclopenten-1-yl, 2-cyclohexen-1-yl, 3-cyclohexen-1-yl, 2-cyclohepten-1-yl, 2-cycloocten-1-yl, 2-cyclononen-1-yl, 2-cyclodecen-1-yl, 2-cyclododecen-1-yl, 2-cycloeicosen-1-yl, 2,4-cyclopentadien-1-yl, 2,4-cyclohexadien-1-yl, 2,5-cyclohexadien-1-yl and the like. Among them, a $C_4$-$C_{12}$ cycloalkenyl group is preferable, and a $C_4$-$C_8$ cycloalkenyl group is particularly preferable.

In the present specification, the "$C_4$-$C_{12}$ cycloalkenyl group" means a cyclic alkenyl group having 4 to 12 carbon atoms, and examples thereof include 2-cyclopenten-1-yl, 3-cyclopenten-1-yl, 2-cyclohexen-1-yl, 3-cyclohexen-1-yl, 2-cyclohepten-1-yl, 2-cycloocten-1-yl, 2-cyclononen-1-yl, 2-cyclodecen-1-yl, 2-cyclododecen-1-yl, 2,4-cyclopentadien-1-yl, 2,4-cyclohexadien-1-yl, 2,5-cyclohexadien-1-yl and the like. Among them, a $C_4$-$C_8$ cycloalkenyl group is preferable.

In the present specification, the "$C_3$-$C_{20}$ cycloalkyl group", "$C_3$-$C_{12}$ cycloalkyl group", "$C_4$-$C_{20}$ cycloalkenyl group" and "$C_4$-$C_{12}$ cycloalkenyl group" are optionally fused with a benzene ring, and examples thereof include 1,2-dihydronaphthalen-1-yl, 1,2-dihydronaphthalen-2-yl, 1,2,3,4-tetrahydronaphthalen-1-yl, 1,2,3,4-tetrahydronaphthalen-2-yl, fluoren-9-yl, inden-1-yl and the like.

In the present specification, the "$C_6$-$C_{20}$ aromatic hydrocarbon group (the $C_5$-$C_{20}$ aryl group)" means a monocyclic or polycyclic (fused) hydrocarbon group having 6 to 20 carbon atoms and showing aromaticity, and examples thereof include phenyl, 1-naphthyl, 2-naphthyl, phenanthryl, anthryl, acenaphthyl, naphthacenyl, biphenylyl and the like. Among them, a $C_6$-$C_{14}$ aromatic hydrocarbon group (a $C_6$-$C_{14}$ aryl group) is preferable, and a $C_6$-$C_{10}$ aromatic hydrocarbon group (a $C_6$-$C_{10}$ aryl group) is particularly preferable.

In the present specification, the "$C_6$-$C_{12}$ aromatic hydrocarbon group (the $C_6$-$C_{12}$ aryl group)" means a monocyclic or polycyclic (fused) hydrocarbon group having 6 to 12 carbon atoms and showing aromaticity, and examples thereof include phenyl, 1-naphthyl, 2-naphthyl, acenaphthyl, biphenylyl and the like. Among them, a $C_6$-$C_{10}$ aromatic hydrocarbon group (a $C_6$-$C_{10}$ aryl group) is preferable.

In the present specification, the "$C_6$-$C_{10}$ aryl group" means a monocyclic or polycyclic (fused) hydrocarbon group having 6 to 10 carbon atoms and showing aromaticity, and examples thereof include phenyl, 1-naphthyl, 2-naphthyl and the like.

In the present specification, the "$C_7$-$C_{14}$ aralkyl group" means a "$C_{1-4}$ alkyl group" substituted by "$C_6$-$C_{10}$ aryl group(s)", and examples thereof include benzyl, 1-phenylethyl, 2-phenylethyl, (naphthyl-1-yl)methyl, (naphthyl-2-yl)methyl, 1-(naphthyl-1-yl)ethyl, 1-(naphthyl-2-yl)ethyl, 2-(naphthyl-1-yl)ethyl, 2-(naphthyl-2-yl)ethyl and the like.

In the present specification, the "$C_1$-$C_{12}$ alkoxy group" means a straight or branched chain alkoxy group having 1 to 12 carbon atoms, and examples thereof include methoxy, ethoxy, propoxy, isopropoxy, butoxy, isobutoxy, sec-butoxy, tert-butoxy, pentyloxy, isopentyloxy, neopentyloxy, hexyloxy, heptyloxy, octyloxy, nonyloxy, decyloxy, undecyloxy, dodecyloxy and the like. Among them, a $C_1$-$C_8$ alkoxy group is preferable, and a $C_1$-$C_4$ alkoxy group is particularly preferable.

In the present specification, the "$C_1$-$C_6$ alkoxy group" means a straight or branched chain alkoxy group having 1 to 6 carbon atoms, and examples thereof include methoxy, ethoxy, propoxy, isopropoxy, butoxy, isobutoxy, sec-butoxy, tert-butoxy, pentyloxy, isopentyloxy, neopentyloxy, hexyloxy and the like. Among them, a $C_1$-$C_4$ alkoxy group is preferable.

In the present specification, the "aromatic heterocyclic group" means a monocyclic or polycyclic (fused) heterocyclic group containing, as a ring-constituting atom besides carbon atom, 1 to 4 hetero atoms selected from an oxygen atom, a sulfur atom and a nitrogen atom, and showing aromaticity.

In the present specification, examples of the "monocyclic aromatic heterocyclic group" include furyl, thienyl, pyridyl, pyrimidinyl, pyridazinyl, pyrazinyl, pyrrolyl, imidazolyl, pyrazolyl, thiazolyl, isothiazolyl, oxazolyl, isoxazolyl, oxadiazolyl (1,2,4-oxadiazolyl, 1,3,4-oxadiazolyl), thiadiazolyl (1,2,4-thiadiazolyl, 1,3,4-thiadiazolyl), triazolyl (1,2,4-triazolyl, 1,2,3-triazolyl), tetrazolyl, triazinyl and the like. Among them, a 5- or 6-membered monocyclic aromatic heterocyclic group is preferable.

In the present specification, the "fused aromatic heterocyclic group" means the above-mentioned monocyclic aromatic heterocyclic group fused with a monocyclic aromatic ring (preferably a benzene ring or a monocyclic aromatic heterocycle), and examples thereof include quinolyl, isoquinolyl, quinazolyl, quinoxalyl, benzofuranyl, benzothienyl, benzoxazolyl, benzisoxazolyl, benzothiazolyl, benzisothiazolyl, benzimidazolyl, benzotriazolyl, indolyl, indazolyl, pyrrolopyridyl, pyrazolopyridyl, imidazopyridyl, thienopyridyl, pyrrolopyrazinyl, pyrazolopyrazinyl, imidazopyrazinyl, thienopyrazinyl, pyrrolopyrimidinyl, pyrazolopyrimidinyl, imidazopyrimidinyl, thienopyrimidinyl, pyrazolothienyl and the like.

In the present specification, examples of the "monocyclic aromatic heterocycle" include furan, thiophene, pyridine, pyrimidine, pyridazine, pyrazine, pyrrole, imidazole, pyrazole, triazole, isothiazole, oxazole, isoxazole, oxadiazole (1,2,4-oxadiazole, 1,3,4-oxadiazole), thiadiazole (1,2,4-thiadiazole, 1,3,4-thiadiazole), triazole (1,2,4-triazole, 1,2,3-triazole), tetrazole, triazine and the like. Among them, a 5- or 6-membered monocyclic aromatic heterocycle is preferable.

In the present specification, the "$C_1$-$C_{12}$ fluorinated alkyl group" means a "$C_{1-12}$ alkyl group" substituted by fluorine atom(s). The number of the fluorine atoms is not particularly limited, and the $C_1$-$C_{12}$ fluorinated alkyl group may be perfluoro-substituted. Specific examples thereof include fluoromethyl, difluoromethyl, trifluoromethyl, 2-fluoroethyl, 2,2-difluoroethyl, 2,2,2-trifluoroethyl, 3-fluoropropyl, 4-fluorobutyl, 5-fluoropentyl, 6-fluorohexyl, 7-fluoroheptyl, 8-fluorooctyl, 9-fluorononyl, 10-fluorodecyl, 11-fluoroundecyl, 12-fluorododecyl and the like.

In the present specification, the "$C_1$-$C_{12}$ fluorinated alkyloxy group" means a "$C_{1-12}$ alkoxy group" substituted by fluorine atom(s). The number of the fluorine atoms is not particularly limited, and the $C_1$-$C_{12}$ fluorinated alkyloxy group may be perfluoro-substituted. Specific examples thereof include fluoromethoxy, difluoromethoxy, trifluoromethoxy, 2-fluoroethoxy, 2,2-difluoroethoxy, 2,2,2-trifluoroethoxy, 3-fluoropropoxy, 4-fluorobutoxy, 5-fluoropentyloxy, 6-fluorohexyloxy, 7-fluoroheptyloxy, 8-fluorooctyloxy, 9-fluorononyloxy, 10-fluorodecyloxy, 11-fluoroundecyloxy, 12-fluorododecyloxy and the like.

In the present specification, the "$C_2$-$C_{13}$ alkoxycarbonyl group" means a group wherein a "$C_1$-$C_{12}$ alkoxy group" is bonded to —C=O—, i.e., a "$C_1$-$C_{12}$ alkoxy-carbonyl group", and examples thereof include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, hexyloxycarbonyl, heptyloxycarbonyl, octyloxycarbonyl, nonyloxycarbonyl, decyloxycarbonyl, undecyloxycarbonyl, dodecyloxycarbonyl and the like. Among them, a $C_2$-$C_9$ alkoxycarbonyl group is preferable, and a $C_2$-$C_5$ alkoxycarbonyl group is particularly preferable.

In the present specification, the "$C_2$-$C_{13}$ acyl group" is a residue obtained by removing a hydroxyl group from a $C_2$-$C_{13}$ carboxylic acid, and it means a "$C_2$-$C_{13}$ aliphatic acyl group" or a "$C_7$-$C_{13}$ aromatic acyl group".

In the present specification, the "$C_2$-$C_{13}$ aliphatic acyl group" means a group wherein a "$C_1$-$C_{12}$ aliphatic hydrocarbon group" is bonded to —C=O—, i.e., a "$C_1$-$C_{12}$ aliphatic hydrocarbon-carbonyl group", and examples thereof include acetyl, propanoyl, butanoyl, 2-methylpropanoyl, pentanoyl, hexanoyl, heptanoyl, octanoyl, nonanoyl, decanoyl, undecanoyl, dodecanoyl, acryloyl, methacryloyl, crotonoyl, isocrotonoyl, propionoyl, cyclopentylcarbonyl, cyclohexylcarbonyl and the like. Among them, a $C_2$-$C_{13}$ alkylcarbonyl group is preferable, and a $C_2$-$C_9$ alkylcarbonyl group is particularly preferable.

In the present specification, the "$C_7$-$C_{13}$ aromatic acyl group" means a group wherein a "$C_6$-$C_{12}$ aromatic hydrocarbon group (a $C_6$-$C_{12}$ aryl group)" is bonded to —C=O—, i.e., a "$C_6$-$C_{12}$ aromatic hydrocarbon (a $C_6$-$C_{12}$ aryl)-carbonyl group", and examples thereof include benzoyl, 1-naphthoyl, 2-naphthoyl and the like.

In the present specification, the "protected amino group" means an amino group protected by a "protecting group". Examples of the "protecting group" include a $C_{1-6}$ alkyl group, a $C_{2-6}$ alkenyl group, a $C_{6-10}$ aryl group, a $C_{7-14}$ aralkyl group, a $C_{1-6}$ alkyl-carbonyl group, a $C_{1-6}$ alkoxy-carbonyl group, a $C_{2-6}$ alkenyl-oxycarbonyl group, a $C_{6-10}$ aryl-carbonyl group, a $C_{7-14}$ aralkyl-carbonyl group, a $C_{6-10}$ aryl-oxycarbonyl group, a $C_{7-14}$ aralkyl-oxycarbonyl group, a $C_{6-10}$ arylsulfonyl group, a benzhydryl group, a trityl group, a tri-$C_{1-6}$ alkylsilyl group, a 9-fluorenylmethyloxycarbonyl group, a phthaloyl group and the like. The above-mentioned protecting group is optionally substituted by a halogen atom, a $C_{1-6}$ alkyl group, a $C_{1-6}$ alkoxy group or a nitro group.

Specific examples of the protecting group include acetyl, trifluoroacetyl, pivaloyl, tert-butoxycarbonyl, 2,2,2-trichloroethoxycarbonyl, benzyloxycarbonyl, 9-fluorenylmethyloxycarbonyl, benzhydryl, trityl, phthaloyl, allyloxycarbonyl, p-toluenesulfonyl, o-nitrobenzenesulfonyl and the like.

In the present specification, the "$C_{1-6}$ alkyl-carbonyl group" means a group wherein a "$C_{1-6}$ alkyl group" is bonded to —C=O—.

In the present specification, the "$C_{1-6}$ alkoxy-carbonyl group" means a group wherein a "$C_{1-6}$ alkoxy group" is bonded to —C=O—.

In the present specification, the "$C_{2-6}$ alkenyl-oxycarbonyl group" means a group wherein a "$C_{2-6}$ alkenyl group" is bonded to the oxygen atom of —C(=O)O—.

In the present specification, the "$C_{6-10}$ aryl-carbonyl group" means a group wherein a "$C_{6-10}$ aryl group" is bonded to —C=O—.

In the present specification, the "$C_{7-14}$ aralkyl-carbonyl group" means a group wherein a "$C_{7-14}$ aralkyl group" is bonded to —C=O—.

In the present specification, the "$C_{6-10}$ aryl-oxycarbonyl group" means a group wherein a "$C_{6-10}$ aryl group" is bonded to the oxygen atom of —C(=O)O—.

In the present specification, the "$C_{7-14}$ aralkyl-oxycarbonyl group" means a group wherein a "$C_{7-14}$ aralkyl group" is bonded to the oxygen atom of —C(=O)O—.

In the present specification, the "$C_{6-10}$ arylsulfonyl group" means a group wherein a "$C_{6-10}$ aryl group" is bonded to —S(=O)$_2$—.

In the present specification, the "tri-$C_{1-6}$ alkylsilyl group" means —SiH$_3$ tri-substituted by "$C_1$-$C_6$ alkyl groups".

In the present specification, the "tri-$C_1$-$C_{12}$ alkylsilyl group" means —SiH$_3$ tri-substituted by "$C_1$-$C_{12}$ alkyl groups".

Each group of the formulas (1)-(7) is explained below.

$R^1$ is a $C_1$-$C_{20}$ hydrocarbon group optionally having substituent(s) selected from Group G1 or a hydrogen atom. The number of the substituents for the $C_1$-$C_{20}$ hydrocarbon group is preferably 1 to 3. When it is 2 or more, these substituents may be the same or different.

$R^1$ is preferably a $C_1$-$C_{20}$ alkyl group optionally having substituent(s) selected from Group G1, a $C_2$-$C_{20}$ alkenyl group optionally having substituent(s) selected from Group G1, a $C_2$-$C_{20}$ alkynyl group optionally having substituent(s) selected from Group G1 or a hydrogen atom, more preferably a $C_1$-$C_{12}$ alkyl group optionally having substituent(s) selected from Group G1, a $C_2$-$C_{12}$ alkenyl group optionally having substituent(s) selected from Group G1, a $C_2$-$C_{12}$ alkynyl group optionally having substituent(s) selected from Group G1 or a hydrogen atom, further more preferably a $C_1$-$C_8$ alkyl group optionally having substituent(s) selected from Group G1, a $C_2$-$C_8$ alkenyl group optionally having substituent(s) selected from Group G1, a $C_2$-$C_8$ alkynyl group optionally having substituent(s) selected from Group G1 or a hydrogen atom, still more preferably a $C_1$-$C_6$ alkyl group optionally having substituent(s) selected from Group G1, a $C_2$-$C_6$ alkenyl group optionally having substituent(s) selected from Group G1, a $C_2$-$C_6$ alkynyl group optionally having substituent(s) selected from Group G1 or a hydrogen atom, still more preferably a $C_1$-$C_6$ alkyl group, a $C_6$-$C_{10}$ aryl-$C_1$-$C_4$ alkyl group (a $C_7$-$C_{14}$ aralkyl group), a $C_2$-$C_6$ alkenyl group, a tri-$C_1$-$C_6$ alkylsilyl-substituted $C_2$-$C_6$ alkynyl group or a hydrogen atom, particularly preferably a $C_1$-$C_6$ alkyl group, a $C_6$-$C_{10}$ aryl-$C_1$-$C_4$ alkyl group (a $C_7$-$C_{14}$ aralkyl group), a $C_2$-$C_6$ alkenyl group or a tri-$C_1$-$C_6$ alkylsilyl-substituted $C_2$-$C_6$ alkynyl group.

$Ar^1$ and $Ar^2$ are each independently a phenyl group optionally having substituent(s) selected from Group G2, a $C_1$-$C_{12}$ chain hydrocarbon group, a $C_3$-$C_{12}$ alicyclic hydrocarbon group or a hydrogen atom. The number of the substituents for the phenyl group is preferably 1 to 3. When it is 2 or more, these substituents may be the same or different.

$Ar^1$ and $Ar^2$ are preferably each independently a phenyl group optionally having substituent(s) selected from Group G2, more preferably each independently a phenyl group optionally having $C_1$-$C_{12}$ fluorinated alkyl group(s), further more preferably each independently a phenyl group optionally having $C_1$-$C_4$ fluorinated alkyl group(s), still more preferably each independently a phenyl group optionally having trifluoromethyl group(s), still more preferably both phenyl groups or both 3,5-bis(trifluoromethyl)phenyl groups, particularly preferably both 3,5-bis(trifluoromethyl)phenyl groups.

$R^5$ is a hydrogen atom, a fluorine atom, a hydroxyl group, a $C_1$-$C_{12}$ alkoxy group, a $C_1$-$C_{12}$ fluorinated alkyloxy group or a silyloxy group represented by —$OSiR^6R^7R^8$ wherein $R^6$, $R^7$ and $R^8$ are each independently a $C_1$-$C_8$ alkyl group or a $C_6$-$C_{20}$ aryl group.

$R^5$ is preferably a hydroxyl group or a silyloxy group represented by —$OSiR^6R^7R^8$ wherein $R^6$, $R^7$ and $R^8$ are as defined above, more preferably a hydroxyl group or a silyloxy group represented by —$OSiR^6R^7R^8$ wherein $R^6$, $R^7$ and $R^8$ are each independently a $C_1$-$C_8$ alkyl group (preferably a methyl group), particularly preferably a hydroxyl group.

Preferable combination of $Ar^1$, $Ar^2$ and $R^5$ is as follows:

(1) An embodiment wherein $Ar^1$ and $Ar^2$ are each independently a phenyl group optionally having substituent(s) selected from Group G2, and $R^5$ is a hydroxyl group.

(2) An embodiment wherein $Ar^1$ and $Ar^2$ are each independently a phenyl group optionally having $C_1$-$C_{12}$ fluorinated alkyl group(s), and $R^5$ is a hydroxyl group.

(3) An embodiment wherein $Ar^1$ and $Ar^2$ are each independently a phenyl group optionally having $C_1$-$C_4$ fluorinated alkyl group(s), and $R^5$ is a hydroxyl group.

(4) An embodiment wherein $Ar^1$ and $Ar^2$ are each independently a phenyl group optionally having trifluoromethyl group(s), and $R^5$ is a hydroxyl group.

(5) An embodiment wherein $Ar^1$ and $Ar^2$ are both phenyl groups or both 3,5-bis(trifluoromethyl)phenyl groups, and $R^5$ is a hydroxyl group.

(6) An embodiment wherein $Ar^1$ and $Ar^2$ are both 3,5-bis(trifluoromethyl)phenyl groups, and $R^5$ is a hydroxyl group.

$R^2$ is a $C_1$-$C_{10}$ alkyl group, or two of $R^2$ in combination form a $C_2$-$C_4$ alkanediyl group optionally having substituent(s) selected from Group G1.

$R^2$ is preferably a $C_1$-$C_4$ alkyl group (particularly methyl).

$R^9$ is a hydrogen atom or a $C_1$-$C_8$ alkyl group.

$R^9$ is preferably a hydrogen atom or a $C_1$-$C_4$ alkyl group (particularly methyl).

$R^{10}$ is a $C_1$-$C_8$ alkyl group.

$R^{10}$ is preferably a $C_1$-$C_4$ alkyl group (particularly ethyl).

In the present invention, optically active 4-chloro-3-hydroxybutanal compound (2) is produced by a step of reacting chloroacetaldehyde with aldehyde compound (1) in the presence of optically active pyrrolidine compound (5) as a catalyst (aldol reaction step).

Chloroacetaldehyde may be used in the form of an aqueous solution. Since chloroacetaldehyde is commercially available in the form of an aqueous solution, it may be used directly.

The amount of aldehyde compound (1) to be used is preferably 0.3-3 mol, more preferably 0.5-2.2 mol, per 1 mol of chloroacetaldehyde, in view of yield, selectivity and economic efficiency.

The catalyst, optically active pyrrolidine compound (5) is preferably a pyrrolidine compound represented by the formula (5a):

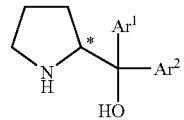

(5a)

wherein $Ar^1$ and $Ar^2$ are as defined above, and the carbon atom marked with * is an asymmetric carbon atom, in view of diastereoselectivity (when $R^1$ in aldehyde compound (1) is not a hydrogen atom), though depending on the kind of aldehyde compound (1). Among them, a pyrrolidine compound wherein $Ar^1$ and $Ar^2$ are each independently a phenyl group optionally having $C_1$-$C_4$ fluorinated alkyl group(s) is preferable, a pyrrolidine compound wherein $Ar^1$ and $Ar^2$ are each independently a phenyl group optionally having trifluoromethyl group(s) is more preferable, a pyrrolidine compound wherein $Ar^1$ and $Ar^2$ are both phenyl groups or both 3,5-bis(trifluoromethyl)phenyl groups is still more preferable, and a pyrrolidine compound wherein $Ar^1$ and $Ar^2$ are both 3,5-bis(trifluoromethyl)phenyl groups is particularly preferable.

The amount of optically active pyrrolidine compound (5) to be used is preferably 0.5-30 mol %, more preferably 1-20 mol %, relative to aldehyde compound (1), in view of yield and economic efficiency.

The aldol reaction of the present invention is preferably carried out in the presence of a solvent containing an organic solvent. Examples of the organic solvent to be used in the present invention include aromatic hydrocarbon solvents (e.g., toluene, benzene, xylene); alcohol solvents (e.g., methanol, ethanol); halogenated hydrocarbon solvents (e.g., chloroform, dichloromethane, carbon tetrachloride); ether solvents (e.g., diethyl ether, tetrahydrofuran); nitrile solvents (e.g., acetonitrile); aprotic polar solvents (e.g., dimethylformamide, dimethylacetamide) and the like. Among them, alcohol solvents, ether solvents, nitrile solvents, aprotic polar solvents are preferable, and ether solvents are particularly preferable in view of good yield, superior enantioselectivity and diastereoselectivity.

When $R^1$ in aldehyde compound (1) is a hydrogen atom, the solvent preferably do not contain water in view of enantioselectivity, though depending on the kind of aldehyde compound (1). In this case, chloroacetaldehyde free of water is preferably used, and chloroacetaldehyde after removing water from commercially available aqueous chloroacetaldehyde solution is used. The water is removed by employing a conventional method (e.g., heated under reflux using the Dean-Stark, etc.).

When $R^1$ in aldehyde compound (1) is not a hydrogen atom, even the solvent contains water, superior enantioselectivity and diastereoselectivity are shown, and mixed solvents of water and an organic solvent selected from an alcohol solvent, an ether solvent, a nitrile solvent and an aprotic polar solvent is preferable, and mixed solvents of an ether solvent and water is particularly preferable, in view of good yield, superior enantioselectivity and diastereoselectivity. When the solvent is a mixed solvent of an ether solvent and water, the amount of water to be used is preferably 0.01-1 mL, more preferably 0.1-0.5 mL, per 1 mL of the ether solvent. When the solvent for the reaction is allowed to contain water, chloroacetaldehyde is used in the form of an aqueous solution.

The amount of the solvent to be used is preferably 1-50 mL, more preferably 3-20 mL, per 1 g of aldehyde compound (1).

The aldol reaction of the present invention is carried out by a method of adding aldehyde compound (1), optically active pyrrolidine compound (5) and a solvent to the solution prepared by dissolving chloroacetaldehyde in a solvent, and then mixing them; a method of adding optically active pyrrolidine compound (5) and a solvent to the solution prepared by dissolving chloroacetaldehyde in a solvent, adding aldehyde compound (1) thereto, and then mixing them; or the like. In view of yield and selectivity, the reaction is preferably carried out by a method of adding aldehyde compound (1), optically active pyrrolidine compound (5) and a solvent to the solution prepared by dissolving chloroacetaldehyde in a solvent, and then mixing them, particularly preferably by a method of adding aldehyde compound (1), optically active pyrrolidine compound (5) and an organic solvent (preferably an organic solvent selected from an alcohol solvent, an ether solvent, a nitrile solvent and an aprotic polar solvent, more preferably an ether solvent) to an aqueous chloroacetaldehyde solution, and then mixing them.

The aldol reaction of the present invention is carried out preferably within the range of 0-100° C., more preferably within the range of 0-40° C., though depending on the kind of aldehyde compound (1).

While the reaction time varies depending on the kind of aldehyde compound (1) and the reaction temperature, it is preferably 1-100 hr, more preferably 10-50 hr, particularly preferably 20-40 hr.

The progress of the reaction can be confirmed by an analysis means such as thin layer chromatography, gas chromatography, high performance liquid chromatography and the like.

Optically active 4-chloro-3-hydroxybutanal compound (2) contained in thus obtained reaction mixture can be isolated by subjecting the reaction mixture to a post-treatment using a conventional method (e.g., neutralization, extraction, washing with water, distillation, crystallization etc.), and purified by subjecting optically active 4-chloro-3-hydroxybutanal compound (2) to recrystallization treatment, extraction purification treatment, distillation treatment, adsorption treatment using activated carbon, silica, alumina and the like, or chromatography treatment using silica gel column chromatography and the like.

4-Chloro-3-hydroxybutanal compound (2) may be isomerized during isolation and/or purification from the reaction mixture. Therefore, the diastereo ratio (syn/anti ratio) and enantiomeric excess (ee(%)) of optically active 4-chloro-3-hydroxybutanal compound (2) are desirably determined without isolation and/or purification after completion of the aldol reaction, but after conversion of optically active 4-chloro-3-hydroxybutanal compound (2) to a compound free of isomerization during reaction, isolation and purification. In the present invention, optically active 4-chloro-3-hydroxybutanal compound (2) is converted to a corresponding optically active acetal compound (an optically active acetal compound represented by the formula (3):

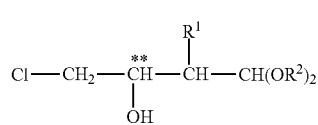

(3)

wherein $R^1$, $R^2$ and ** are as defined above), or a corresponding optically active α,β-unsaturated ester compound (an optically active α,β-unsaturated ester compound represented by the formula (4):

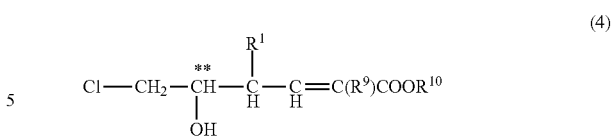

(4)

wherein $R^1$, $R^9$, $R^{10}$ and ** are as defined above).

Optically active acetal compound (3) is produced by a step of subjecting optically active 4-chloro-3-hydroxybutanal compound (2) to acetalization (acetalization reaction step).

Specifically, optically active acetal compound (3) is produced by a step of reacting optically active 4-chloro-3-hydroxybutanal compound (2) with an acetalizating agent corresponding to $R^2$ (e.g., $R^2OH$, $HC(OR^2)_3$, $(CH_3)_2C(OR^2)_2$) in the presence of an acid catalyst.

Optically active acetal compound (3) is preferably produced by a step of reacting the reaction mixture after completion of the aldol reaction which contains optically active 4-chloro-3-hydroxybutanal compound (2) with an acetalizating agent corresponding to $R^2$ (e.g., $R^2OH$, $HC(OR^2)_3$, $(CH_3)_2C(OR^2)_2$) in the presence of an acid catalyst.

Optically active acetal compound (3) is more preferably produced by a step of reacting the reaction mixture after completion of the aldol reaction which contains optically active 4-chloro-3-hydroxybutanal compound (2) with $HC(OR^2)_3$, wherein $R^2$ is a $C_1$-$C_8$ alkyl group in the presence of an acid catalyst.

The amount of $HC(OR^2)_3$ to be used is preferably 1-20 mol, more preferably 3-10 mol, per 1 mol of optically active 4-chloro-3-hydroxybutanal compound (2), in view of yield and economic efficiency.

Examples of the acid catalyst to be used include p-toluenesulfonic acid and a hydrate thereof (monohydrate), and p-pyridinium toluenesulfonate. Among them, p-toluenesulfonic acid and a hydrate thereof (monohydrate) are preferable, in view of yield and economic efficiency.

The amount of the acid catalyst to be used is preferably 0.01-1 mol, more preferably 0.01-0.1 mol, per 1 mol of optically active 4-chloro-3-hydroxybutanal compound (2), in view of reaction rate.

The above-mentioned acetalization reaction is carried out by a method of adding $HC(OR^2)_3$ and an acid catalyst to the reaction mixture after completion of the aldol reaction which contains optically active 4-chloro-3-hydroxybutanal compound (2), and then mixing them; a method of adding an acid catalyst to the reaction mixture after completion of the aldol reaction which contains optically active 4-chloro-3-hydroxybutanal compound (2), adding $HC(OR^2)_3$ thereto, and then mixing them; or the like. In view of convenient operation, the reaction is preferably carried out by a method of adding $HC(OR^2)_3$ and an acid catalyst to the reaction mixture after completion of the aldol reaction which contains optically active 4-chloro-3-hydroxybutanal compound (2), and then mixing them.

The acetalization reaction is carried out preferably within the range of 0-100° C., more preferably within the range of 10-40° C., particularly preferably within the range of 20-30° C., though depending on the kind of $HC(OR^2)_3$ and the acid catalyst.

While the reaction time varies depending on the kind of $HC(OR^2)_3$ and the acid catalyst, and the reaction temperature, it is preferably 10 min-50 hr, more preferably 30 min-20 hr, particularly preferably 1-10 hr.

The progress of the reaction can be confirmed by an analysis means such as thin layer chromatography, gas chromatography, high performance liquid chromatography and the like.

Optically active acetal compound (3) contained in thus obtained reaction mixture can be isolated by subjecting the reaction mixture to a post-treatment using a conventional method (e.g., neutralization, extraction, washing with water, distillation, crystallization etc.), and purified by subjecting optically active acetal compound (3) to recrystallization treatment, extraction purification treatment, distillation treatment, adsorption treatment using activated carbon, silica, alumina and the like, or chromatography treatment using silica gel column chromatography and the like.

Optically active α,β-unsaturated ester compound (4) is produced by a step of reacting optically active 4-chloro-3-hydroxybutanal compound (2) with $Ph_3P=C(R^9)CO_2R^{10}$ wherein Ph, $R^9$ and $R^{10}$ are as defined above (Wittig reaction step).

Optically active α,β-unsaturated ester compound (4) is preferably produced by a step of reacting the reaction mixture after completion of the aldol reaction which contains optically active 4-chloro-3-hydroxybutanal compound (2) with $Ph_3P=C(R^9)CO_2R^{10}$ wherein Ph, $R^9$ and $R^{10}$ are as defined above.

The amount of $Ph_3P=C(R^9)CO_2R^{10}$ to be used is preferably 0.01-5 mol, more preferably 0.5-2 mol, per 1 mol of optically active 4-chloro-3-hydroxybutanal compound (2), in view of yield and economic efficiency.

The above-mentioned Wittig reaction is carried out by a method of adding $Ph_3P=C(R^9)CO_2R^{10}$ to the reaction mixture after completion of the aldol reaction which contains optically active 4-chloro-3-hydroxybutanal compound (2), and then mixing them; a method of adding the reaction mixture after completion of the aldol reaction which contains optically active 4-chloro-3-hydroxybutanal compound (2) to $Ph_3P=C(R^9)CO_2R^{10}$, and then mixing them; or the like. In view of convenient operation, the reaction is preferably carried out by a method of adding $Ph_3P=C(R^9)CO_2R^{10}$ to the reaction mixture after completion of the aldol reaction which contains optically active 4-chloro-3-hydroxybutanal compound (2), and then mixing them.

The above-mentioned Wittig reaction is carried out preferably within the range of 0-100° C., more preferably within the range of 10-40° C., particularly preferably within the range of 20-30° C., though depending on the kind of $Ph_3P=C(R^9)CO_2R^{10}$.

While the reaction time varies depending on the kind of $Ph_3P=C(R^9)CO_2R^{10}$ and the reaction temperature, it is preferably 10 min-50 hr, more preferably 30 min-20 hr, particularly preferably 1-10 hr.

The progress of the reaction can be confirmed by an analysis means such as thin layer chromatography, gas chromatography, high performance liquid chromatography and the like.

Optically active α,β-unsaturated ester compound (4) contained in thus obtained reaction mixture can be isolated by subjecting the reaction mixture to a post-treatment using a conventional method (e.g., neutralization, extraction, washing with water, distillation, crystallization etc.), and purified by subjecting optically active α,β-unsaturated ester compound (4) to recrystallization treatment, extraction purification treatment, distillation treatment, adsorption treatment using activated carbon, silica, alumina and the like, or chromatography treatment using silica gel column chromatography and the like.

The diastereo ratio (syn/anti ratio) and enantiomeric excess of the obtained optically active acetal compound (3) or optically active α,β-unsaturated ester compound (4) are determined. The measured diastereo ratio (syn/anti ratio) and enantiomeric excess correspond to those of optically active 4-chloro-3-hydroxybutanal compound (2).

When $R^1$ in aldehyde compound (1) is not a hydrogen atom, in the aldol reaction step of the present invention, the anti-form of optically active 4-chloro-3-hydroxybutanal compound (2) is preferentially obtained. The diastereoselectivity showing a diastereo ratio (syn/anti ratio) of, for example, 50/50 or more, or, for example, 20/80 or more, is available.

In the aldol reaction step of the present invention, when pyrrolidine compound (5a) wherein the absolute configuration of C* is S-configuration, i.e., a pyrrolidine compound represented by the formula (5a-S):

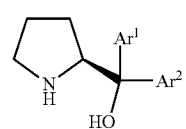

(5a-S)

wherein $Ar^1$ and $Ar^2$ are as defined above,
is used as a catalyst, optically active 4-chloro-3-hydroxybutanal compound (2) wherein the absolute configuration of C** is R-configuration, i.e., an optically active 4-chloro-3-hydroxybutanal compound represented by the formula (2R):

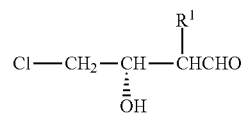

(2R)

wherein $R^1$ is as defined above,
is preferentially obtained.

On the other hand, when pyrrolidine compound (5a) wherein the absolute configuration of C* is R-configuration, i.e., a pyrrolidine compound represented by the formula (5a-R):

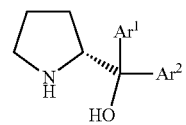

(5a-R)

wherein $Ar^1$ and $Ar^2$ are as defined above,
is used as a catalyst, optically active 4-chloro-3-hydroxybutanal compound (2) wherein the absolute configuration of C** is S-configuration, i.e., an optically active 4-chloro-3-hydroxybutanal compound represented by the formula (2S):

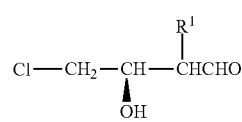

(2S)

wherein $R^1$ is as defined above,
is preferentially obtained.

Therefore, in the aldol reaction step of the present invention, the enantioselectivity showing an enantiomeric excess of, for example, 50 ee % or more, or, for example, 80 ee % or more, is available.

In optically active acetal compound (3) and optically active α,β-unsaturated ester compound (4), the chlorine atom and the hydroxy group are separately bonded to the adjacent carbon atoms. Accordingly, by reacting optically active acetal compound (3) or optically active α,β-unsaturated ester compound (4) with a base, corresponding optically active epoxy compound (6) or (7) can be easily produced. Optically active epoxy compound (6) or (7) is extremely useful as a reactive intermediate for production of pharmaceutical products.

Optically Active Epoxy Compound (6)

A corresponding optically active epoxy compound (an optically active epoxy compound represented by the formula (6):

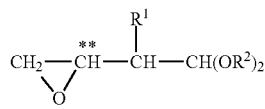

(6)

wherein $R^1$, $R^2$ and ** are as defined above,
is produced by a step of reacting optically active acetal compound (3) with a base (epoxidation reaction step).

Examples of the base include alkali metal carbonates such as potassium carbonate, sodium carbonate and the like; metal alcolates such as sodium methylate and the like, and the like. Among them, potassium carbonate is preferable in view of yield and economic efficiency.

The amount of the base to be used is preferably 0.8-2 mol, more preferably 1-1.5 mol, per 1 mol of optically active acetal compound (3), in view of yield and economic efficiency.

The epoxidation reaction of the present invention is preferably carried out in a solvent. Examples of the solvent include alcohol solvents (e.g., methanol, ethanol); ether solvents (e.g., diethyl ether, methyl t-butyl ether, tetrahydrofuran) and the like. Among them, alcohol solvents are preferable in view of yield.

The epoxidation reaction of the present invention is preferably carried out by a method of adding a base to the solution prepared by dissolving optically active acetal compound (3) in a solvent, in view of convenient operation. The addition of the base is carried out preferably within the range of −20-20° C., more preferably within the range of −10-10° C.

The epoxidation reaction of the present invention is preferably carried out by reacting the reaction mixture after completion of the acetalization reaction which contains optically active acetal compound (3) with a base, in view of convenient operation.

The epoxidation reaction of the present invention is carried out preferably within the range of 0-120° C., more preferably within the range of 40-80° C., though depending on the kind of optically active acetal compound (3).

While the reaction time varies depending on the kind of optically active acetal compound (3) and the reaction temperature, it is preferably 1-100 hr, more preferably 1-20 hr.

The progress of the reaction can be confirmed by an analysis means such as thin layer chromatography, gas chromatography, high performance liquid chromatography and the like.

Optically Active Epoxy Compound (7)

A corresponding optically active epoxy compound (an optically active epoxy compound represented by the formula (7):

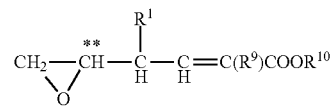

(7)

wherein $R^1$, $R^9$, $R^{10}$ and ** are as defined above,
is produced by a step of reacting optically active α,β-unsaturated ester compound (4) with a base (epoxidation reaction step).

Examples of the base include alkali metal carbonates such as potassium carbonate, sodium carbonate and the like; metal alcolates such as sodium methylate and the like, and the like. Among them, potassium carbonate is preferable in view of yield and economic efficiency.

The amount of the base to be used is preferably 0.5-2 mol, more preferably 0.8-1.3 mol, per 1 mol of optically active α,β-unsaturated ester compound (4), in view of yield and economic efficiency.

The epoxidation reaction of the present invention is preferably carried out in a solvent. Examples of the solvent include alcohol solvents (e.g., methanol, ethanol); ether solvents (e.g., diethyl ether, methyl t-butyl ether, tetrahydrofuran) and the like. Among them, alcohol solvents are preferable in view of yield.

The epoxidation reaction of the present invention is preferably carried out by a method of adding a base to the solution prepared by dissolving optically active α,β-unsaturated ester compound (4) in a solvent, in view of convenient operation. The addition of the base is carried out preferably within the range of −20-20° C., more preferably within the range of −10-10° C.

The epoxidation reaction of the present invention is preferably carried out by reacting the reaction mixture after completion of the reaction which contains optically active α,β-unsaturated ester compound (4) with a base, in view of convenient operation.

The epoxidation reaction of the present invention is carried out preferably within the range of 0-120° C., more preferably within the range of 40-80° C., though depending on the kind of optically active α,β-unsaturated ester compound (4).

While the reaction time varies depending on the kind of optically active α,β-unsaturated ester compound (4) and the reaction temperature, it is preferably 1-100 hr, more preferably 1-20 hr.

The progress of the reaction can be confirmed by an analysis means such as thin layer chromatography, gas chromatography, high performance liquid chromatography and the like.

EXAMPLE

The present invention is explained in detail in the following by referring to Examples.

Chloroacetaldehyde (ca. 40% in water, ca. 6.1 mol/L, catalog number: C0083), which was purchased from TCI (Tokyo Chemical Industry Co., LTD.) was used directly.

All liquid aldehydes and solvents were distilled before use except chloroacetaldehyde.

All reaction were carried out under argon atmosphere and monitored by thin-layer chromatography using Merck 60 F254 precoated silica gel plates (0.25 mm thickness). Preparative thin layer chromatography was performed using Wakogel B-5F purchased from Wako Pure Chemical Industries (Tokyo, Japan). Flush chromatography was performed using silica gel 60N of Kanto Chemical Co. Int. (Tokyo Japan).

FT-IR spectra were recorded on a JASCO FT/IR-410 spectrometer.

$^1$H and $^{13}$C NMR spectra were recorded on a Bruker AM400 (400 MHz for $^1$H NMR, 100 MHz for $^{13}$C NMR) instrument. Data for $^1$H NMR are reported as chemical shift (δppm), multiplicity (s=singlet, d=doublet, t=triplet, q=quartet, m=multiplet), coupling constant (Hz), integration and assignment. Data for $^{13}$C NMR are reported as chemical shift.

High-resolution mass spectral analyses (HRMS) were carried out using Bruker ESI-TOF MS.

HPLC analysis was performed on a HITACHI Elite LaChrom Series HPLC, while UV detection was monitored at appropriate wavelength respectively, using CHIRALCEL OD-H (0.46 cm×25 cm), CHIRALCEL OJ-H (0.46 cm×25 cm), CHIRALPAK IA column (0.46 cm×25 cm), CHIRALPAK IC column (0.4 cm×1 cm), CHIRALPAK AD-H (0.46 cm×25 cm) and CHIRALPAK AS-H (0.46 cm×25 cm).

Examples 1-1-1-4

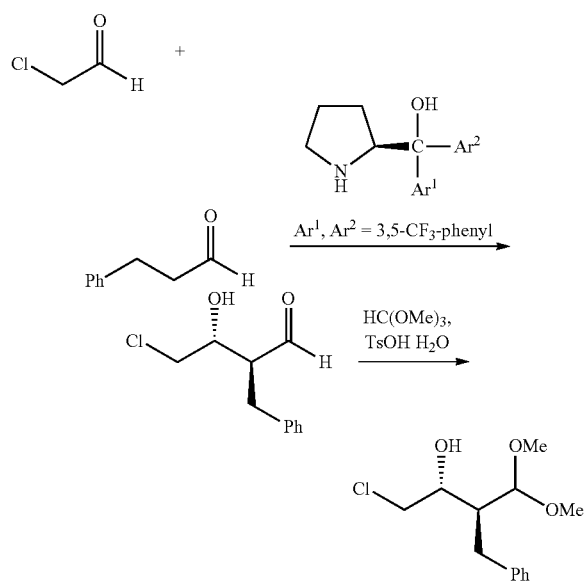

To a 40% aqueous chloroacetaldehyde solution (0.75 mmol, 123 μL) were added (S)-2-[bis(3,5-bis-trifluoromethylphenyl)hydroxymethyl]pyrrolidine (0.05 mmol, 10 mol % relative to 3-phenylpropanal), the solvent shown in Table 1 (0.5 mL) and 3-phenylpropanal (aldehyde compound (1), 0.5 mmol). The reaction mixture was stirred at 23° C. for the time shown in Table 1, trimethyl orthoformate (6.0 mmol) and p-toluenesulfonic acid monohydrate (0.1 mmol) were added thereto, and the mixture was stirred at 23° C. for 1 hr. The acetalization reaction was quenched by the addition of saturated aqueous sodium hydrogen carbonate solution. The organic materials were extracted with chloroform (threetimes), and the extract was dried over anhydrous MgSO$_4$, filtered, and concentrated under reduced pressure. The residue was purified by column chromatography (ethyl acetate:hexane=1:6) to give (2R,3S)-3-benzyl-1-chloro-4,4-dimethoxybutan-2-ol. The yield, syn/anti ratio and enantiomeric excess are shown in Table 1. The yield was calculated as a yield over two steps. The syn/anti ratio was determined by $^1$H-NMR spectrum. The enantiomeric excess was determined by HPLC equipped with CHIRALPAK AD-H column ($^i$PrOH:hexane=1:100) (0.25 mL/min, the retention time of the minor enantiomer=32.1 min, the retention time of the major enantiomer=41.8 min) after conversion to the corresponding 3,5-dinitrobenzoate.

TABLE 1

| Example | Solvent | Time (hr) | Yield (%) | anti:syn | ee % |
|---|---|---|---|---|---|
| 1-1 | THF | 82 | 72 | 3.9:1 | 99 |
| 1-2 | DMF | 60 | 75 | 2.8:1 | 95 |
| 1-3 | MeOH | 48 | 52 | 3.0:1 | 94 |
| 1-4 | CH$_3$CN | 60 | 60 | 4.0:1 | 94 |

Examples 2-1-2-8

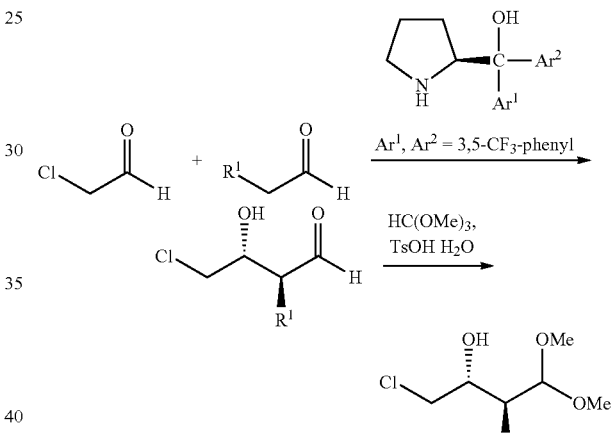

To a 40% aqueous chloroacetaldehyde solution (the amount (X) shown in Table 2) were added (S)-2-[bis(3,5-bis-trifluoromethylphenyl)hydroxymethyl]pyrrolidine (0.05 mmol, except that 0.075 mmol was used in Examples 2-4, 2-6 and 2-7), THF (0.5 mL) and aldehyde compound (1) (the amount (Y) shown in Table 2). The reaction mixture was stirred at 23° C. for the time shown in Table 2, trimethyl orthoformate (492 μL, 4.5 mmol) and p-toluenesulfonic acid monohydrate (19.0 mg, 0.1 mmol) were added thereto, and the mixture was stirred at 23° C. for 1 hr. The reaction was quenched by the addition of saturated aqueous sodium hydrogen carbonate solution. The organic materials were extracted with chloroform (threetimes), and the extract was dried over anhydrous MgSO$_4$, filtered, and concentrated under reduced pressure. The residue was purified by column chromatography (ethyl acetate:hexane=1:6) to give acetal compound (3) (R$^2$=methyl). The yield, syn/anti ratio and enantiomeric excess are shown in Table 2. The yield was calculated as a yield over two steps. The syn/anti ratio was determined by $^1$H-NMR spectrum. The enantiomeric excess was determined by HPLC equipped with chiral column after conversion to the corresponding p-nitrobenzoate or 3,5-dinitrobenzoate, as necessary.

(2R,3S)-1-chloro-4,4-dimethoxy-3-methylbutan-2-ol (Example 2-1)

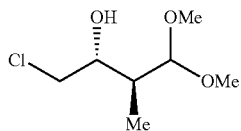

as diastereomer mixture (anti:syn=5.88:1);

$^1$H NMR (CDCl$_3$, 400 MHz): δ0.94 (3H, d, J=6.8 Hz), 2.08-2.16 (1H, m), 3.40 (3H, s), 3.45 (3H, s), 3.61 (1H, dd, J=5.2, 11.6 Hz), 3.66 (1H, br-s), 3.74 (1H, dd, J=3.2, 11.6 Hz), 3.82-3.86 (1H, m), 4.36 (1H, d, J=5.2 Hz);

$^{13}$C NMR (CDCl$_3$, 100 MHz): δ11.0, 38.7, 48.6, 54.1, 56.3, 72.3, 108.1;

IR (neat): ν$_{max}$ 3456, 2935, 2835, 1459, 1384, 1281, 1194, 1107, 1060, 943, 751, 536 cm$^{-1}$;

HRMS (ESI): [M+Na]$^+$ calculated for ([C$_7$H$_{15}$ClO$_3$Na]$^+$): 205.0602. found: 205.0593; The enantiomeric excess was determined by HPLC equipped with CHIRALPAK IC column ($^i$PrOH:hexane=1:80) (1 mL/min, the retention time of the major enantiomer=20.2 min, the retention time of the minor enantiomer=23.6 min) after p-nitrobenzoylation of the acetalization product.

(2R,3S)-1-chloro-3-(dimethoxymethyl)pentan-2--ol (Example 2-2)

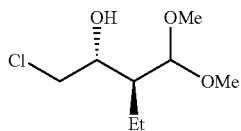

as diastereomer mixture (anti:syn=9.0:1);

$^1$H NMR (CDCl$_3$, 400 MHz): δ0.97 (3H, t, J=7.6 Hz), 1.47-1.55 (2H, m), 1.91 (1H, ddt, J=4.4, 6.4, 12.0 Hz), 3.41 (3H, s), 3.45 (3H, s), 3.67 (1H, dd, J=6.2, 11.4 Hz), 3.72 (1H, dd, J=4.4, 11.2 Hz), 3.95 (1H, dd, J=5.6, 10.8 Hz), 4.43 (1H, d, J=4.0 Hz);

$^{13}$C NMR (CDCl$_3$, 100 MHz): 611.7, 19.7, 44.2, 48.6, 54.8, 56.6, 71.2, 107.8;

IR (neat): ν$_{max}$ 3483, 2964, 2834, 1465, 1374, 1281, 1176, 1140, 1068, 845, 683, 405 cm$^{-1}$;

HRMS (ESI): [M+Na]$^+$ calculated for ([C$_8$H$_{17}$ClO$_3$Na]$^+$): 219.0758. found: 219.0760; The enantiomeric excess was determined by HPLC equipped with CHIRALPAK IC column ($^i$PrOH:hexane=1:50) (1 mL/min, the retention time of the major enantiomer-38.3 min, the retention time of the minor enantiomer=42.2 min) after 3,5-dinitrobenzoylation of the acetalization product.

(2R,3S)-1-chloro-3-(dimethoxymethyl)hexan-2-ol (Example 2-3)

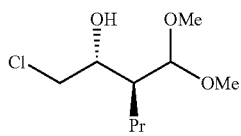

as diastereomer mixture (anti:syn=5.88:1);

$^1$H NMR (CDCl$_3$, 400 MHz): δ0.92 (3H, t, J=7.0 Hz), 1.32-1.45 (4H, m), 1.96-2.02 (1H, m), 3.41 (3H,$), 3.44 (3H, $), 3.51 (1H, d, J=5.2 Hz), 3.71 (1H, dd, J=4.8, 11.2 Hz), 3.92 (1H, quin., J=5.2 Hz), 4.40 (1H, d, J=4.0 Hz);

$^{13}$C NMR (CDCl$_3$, 100 MHz): δ14.3, 20.5, 28.8, 42.4, 48.5, 55.1, 56.5, 72.0, 108.0;

IR (neat): ν$_{max}$ 3481, 2959, 1457, 1377, 1190, 1109, 1063, 967, 732, 437, 419 cm$^{-1}$;

HRMS (ESI): [M+Na]$^+$ calculated for ([C$_9$H$_{19}$ClO$_3$Na]$^+$): 233.0915. found: 233.0926; The enantiomeric excess was determined by HPLC equipped with CHIRALPAK IC column ($^i$PrOH:hexane=1:50) (1 mL/min, the retention time of the major enantiomer=35.1 min, the retention time of the minor enantiomer-39.6 min) after 3,5-dinitrobenzoylation of the acetalization product.

(2R,3S)-1-chloro-3-(dimethoxymethyl)-4-methylpentan-2-ol (Example 2-4)

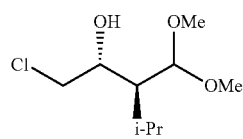 [SMILES: COC(OC)[C@@H](C(C)C)[C@@H](O)CCl]

as diastereomer mixture (anti:syn=9.09:1);

$^1$H NMR (CDCl$_3$, 400 MHz): δ0.97 (3H, d, J=6.8 Hz), 1.03 (3H, d, J=6.8 Hz), 1.74-1.78 (1H, m), 1.93-2.02 (1H, m), 3.39 (3H, s), 3.45 (3H, s), 3.72 (2H, d, J=6.0 Hz), 4.00 (1H, ddd, J=4.0, 6.0, 14.2 Hz), 4.50 (1H, d, J=4.0 Hz);

$^{13}$C NMR (CDCl$_3$, 100 MHz): δ20.3, 20.6, 26.9, 47.6, 49.6, 54.6, 56.5, 71.2, 107.5;

IR (neat): ν$_{max}$ 3485, 2962, 2839, 2360, 1459, 1112, 1061, 916, 428, 414 cm$^{-1}$;

HRMS (ESI): [M+Na]$^+$ calculated for ([C$_9$H$_{19}$ClO$_3$Na]$^+$): 233.0915. found: 233.0924; The enantiomeric excess was determined by HPLC equipped with CHIRALPAK IC column ($^i$PrOH:hexane=1:50) (1 mL/min, the retention time of the major enantiomer=28.6 min, the retention time of the minor enantiomer=30.7 min) after 3,5-dinitrobenzoylation of the acetalization product

(2R,3S)-3-benzyl-1-chloro-4,4-dimethoxybutan-2-ol (Example 2-5)

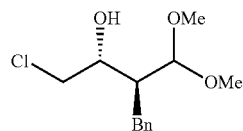 [SMILES: COC(OC)[C@@H](Cc1ccccc1)[C@@H](O)CCl]

as diastereomer mixture (anti:syn=3.85:1);

$^1$H NMR (CDCl$_3$, 400 MHz): δ2.30-2.36 (1H, m), 2.75 (1H, dd, J=8.0, 14.0 Hz), 2.81 (1H, dd, J=8.0, 13.6 Hz), 3.36 (3H, s), 3.45 (3H, s), 3.58 (1H, d, J=5.2 Hz), 3.68 (1H, d, J=2.0 Hz), 3.70 (1H, s), 3.91 (1H, quin., J=5.2 Hz), 4.28 (1H, d, J=2.8 Hz), 7.20-7.32 (5H, m);

$^{13}$C NMR (CDCl$_3$, 100 MHz): δ33.0, 44.6, 48.5, 55.6, 56.8, 71.4, 107.4, 126.3, 128.6, 129.1, 139.6;

IR (neat): ν$_{max}$ 3493, 3027, 2946, 2834, 2360, 1603, 1496, 1454, 1370, 1281, 1189, 1123, 1060, 963, 752, 702, 499 cm$^{-1}$;

HRMS (ESI): [M+Na]$^+$ calculated for ([C$_{13}$H$_{19}$ClO$_3$Na]$^+$): 281.0915. found: 281.0926;

The enantiomeric excess was determined by HPLC equipped with CHIRALPAK AD-H column ($^i$PrOH:hexane=1:100) (0.25 mL/min, the retention time of the minor enantiomer=32.1 min, the retention time of the major enantiomer=41.8 min).

(2R,3S,Z)-1-chloro-3-(dimethoxymethyl)non-6-en-2-ol (Example 2-6)

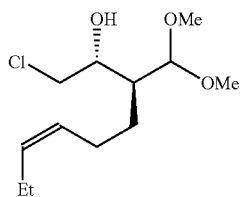 [SMILES: CC/C=C\CC[C@H](C(OC)OC)[C@@H](O)CCl]

as diastereomer mixture (anti:syn=5.88:1);

$^1$H NMR (CDCl$_3$, 400 MHz): δ0.97 (3H, t, J=7.6 Hz), 1.44-1.55 (2H, m), 1.99-2.17 (5H, m), 3.41 (3H, s), 3.45 (3H, s), 3.51 (1H, d, J=5.6 Hz), 3.65-3.74 (2H, m), 3.94 (1H, quin., J=5.4 Hz), 4.41 (1H, d, J=4.0 Hz), 5.27-5.44 (2H, m);

$^{13}$C NMR (CDCl$_3$, 100 MHz): δ14.4, 20.7, 24.8, 26.5, 42.1, 48.4, 55.3, 56.5, 71.9, 108.0, 128.5, 132.6;

IR (neat): ν$_{max}$ 3734, 3648, 3500, 2963, 2361, 1558, 1541, 1457, 1067, 668, 484, 463, 420 cm$^{-1}$;

HRMS (ESI): [M+Na]$^+$ calculated for ([C$_{12}$H$_{23}$ClO$_3$Na]$^+$): 273.1228. found: 273.1228;

The enantiomeric excess was determined by HPLC equipped with CHIRALPAK IC column ($^i$PrOH:hexane=1:80) (1 mL/min, the retention time of the major enantiomer=33.4 min, the retention time of the minor enantiomer=37.4 min) after p-nitrobenzoylation of the acetalization product.

(2R,3S)-1-chloro-3-(dimethoxymethyl)-6-(trimethylsilyl)hex-5-yn-2-ol (Example 2-7)

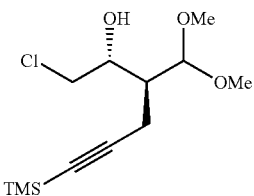 [SMILES: COC(OC)[C@@H](CC#C[Si](C)(C)C)[C@@H](O)CCl]

as diastereomer mixture (anti:syn=3.0:1);

$^1$H NMR (CDCl$_3$, 400 MHz): δ0.15 (9H, s), 2.18 (1H, ddd, J=6.0, 8.0, 10.0 Hz), 2.43 (2H, d, J=6.4 Hz), 3.42 (3H, s), 3.47 (3H, s), 3.62 (1H, d, J=4.0 Hz), 3.73 (1H, dd, J=5.6, 11.6 Hz), 3.79 (1H, dd, J=4.0, 11.6 Hz), 4.62 (1H, d, J=5.6 Hz);

$^{13}$C NMR (CDCl$_3$, 100 MHz): δ0.00, 18.1, 42.0, 48.1, 54.7, 56.1, 71.3, 97.0, 101.4, 106.4;

IR (neat): ν$_{max}$ 3447, 2954, 2925, 2175, 1714, 1457, 1281, 1250, 1178, 1141, 1069, 844, 760, 683, 419, 405 cm$^{-1}$;

HRMS (ESI): [M+Na]$^+$ calculated for ([C$_{12}$H$_{23}$ClO$_3$SiNa]$^+$): 301.0997. found: 301.0986;

The enantiomeric excess was determined by HPLC equipped with CHIRALPAK IC column ($^i$PrOH:hexane=1:30) (1 mL/min, the retention time of the major enantiomer=15.1 min, the retention time of the minor enantiomer-17.0 min) after 3,5-dinitrobenzoylation of the acetalization product.

(R)-1-chloro-4,4-dimethoxybutan-2-ol (Example 2-8)

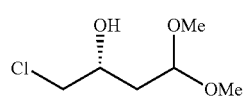

$^1$H NMR (CDCl$_3$, 400 MHz): δ1.86-1.90 (2H, m), 3.05 (1H, br-d, J=3.2 Hz), 3.38 (3H, s), 3.38 (3H, s), 3.53-3.57 (2H, m), 4.00-4.02 (1H, m), 4.61 (1H, t, J=5.6 Hz);

$^{13}$C NMR (CDCl$_3$, 100 MHz): δ36.8, 49.4, 53.5, 53.9, 68.4, 103.3;

IR (neat): ν$_{max}$ 3450, 2963, 2835, 1727, 1648, 1447, 1374, 1281, 1189, 1128, 1057, 962, 902, 822, 745, 683, 409 cm$^{-1}$;

HRMS (ESI): [M+Na]$^+$ calculated for ([C$_6$H$_{13}$ClO$_3$Na]$^+$): 191.0445. found: 191.0441;

[α]$_D^{22}$=−9.72° (c=1.80, CHCl$_3$);

The enantiomeric excess was determined by HPLC equipped with CHIRALPAK AD-H column ($^i$PrOH:hexane=1:30) (1 mL/min, the retention time of the major enantiomer=17.4 min, the retention time of the minor enantiomer=12.9 min) after 3,5-dinitrobenzoylation of the acetalization product.

TABLE 2

| Example | Product | X (mmol) | Y (mmol) | Time (hr) | Yield (%) | anti:syn | ee (%) |
|---------|---------|----------|----------|-----------|-----------|----------|--------|
| 2-1 | ![structure with Me] | 0.5 | 1.0 | 33 | 90 | 5.9:1 | 95 |
| 2-2 | ![structure with Et] | 0.5 | 1.0 | 38 | 81 | 9.0:1 | 97 |

TABLE 2-continued

| Example | Product | X (mmol) | Y (mmol) | Time (hr) | Yield (%) | anti:syn | ee (%) |
|---|---|---|---|---|---|---|---|
| 2-3 | (structure with Pr) | 0.5 | 1.0 | 36 | 82 | 5.9:1 | 98 |
| 2-4 | (structure with i-Pr) | 0.5 | 1.0 | 90 | 68 | 9.1:1 | 97 |
| 2-5 | (structure with Bn) | 0.75 | 0.5 | 82 | 72 | 3.9:1 | 99 |
| 2-6 | (structure with cis-CH2CH=CHEt) | 0.75 | 0.5 | 46 | 76 | 5.9:1 | 98 |
| 2-7 | (structure with CH2C≡C-TMS) | 0.75 | 0.5 | 86 | 66 | 3.0:1 | 90 |
| 2-8 | (structure, no R) | 0.5 | 1.5 | 24 | 71 | — | 60 |

Examples 3-1-3-6

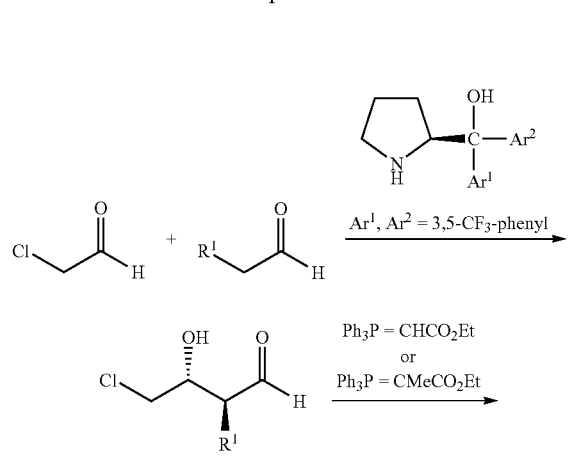

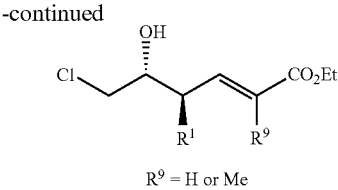

$R^9$ = H or Me

To a 40% aqueous chloroacetaldehyde solution (the amount (X) shown in Table 3) were added (S)-2-[bis(3,5-bis-trifluoromethylphenyl)hydroxymethyl]pyrrolidine (0.05 mmol, except that 0.075 mmol was used in Examples 3-4 and 3-6), THF (0.5 mL) and aldehyde compound (1) (the amount (Y) shown in Table 3). The reaction mixture was stirred at 23° C. for the time shown in Table 3, the Wittig reagent (435 mg, 1.25 mmol) was added thereto, and the mixture was stirred at 23° C. for 1 hr. The Wittig reaction was quenched by through silica gel pad, and concentrated under reduced pressure. The residue was purified by preparative thin layer chromatography (ethyl acetate:hexane=1:5) to give α,β-unsaturated ester compound (4) ($R^9$=a hydrogen atom or methyl, and $R^{10}$=ethyl). The yield, syn/anti ratio and enantiomeric excess are shown in Table 3. The yield was calculated as a yield over two steps. The syn/anti ratio was determined by $^1$H-NMR spectrum. The enantiomeric excess was determined by HPLC equipped with chiral column after convertion to the corresponding 3,5-dinitrobenzoate.

(4R,5R,E)-ethyl 6-chloro-5-hydroxy-4-methylhex-2-enoate (Example 3-1)

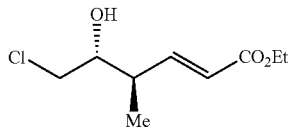

as diastereomer mixture (anti:syn=4.19:1);

$^1$H NMR (CDCl$_3$, 400 MHz): δ1.14 (3H, t, J=6.8 Hz), 1.29 (3H, t, J=7.2 Hz), 2.25 (1H, d, J=4.8 Hz), 2.58-2.64 (1H, m), 3.53 (1H, dd, J=7.4, 11.4 Hz), 3.63 (1H, dd, J=3.6, 11.2 Hz), 3.72-3.77 (1H, m), 4.19 (2H, q, J=7.2 Hz), 5.90 (1H, dd, J=1.0, 15.8 Hz), 6.96 (1H, dd, J=8.4, 15.6 Hz);

$^{13}$C NMR (CDCl$_3$, 100 MHz): δ14.4, 16.0, 40.2, 48.4, 60.6, 74.5, 122.7, 149.0, 166.6;

IR (neat): $v_{max}$ 3462, 2982, 2927, 2876, 1702, 1652, 1370, 1280, 1183, 1034, 985, 869 cm$^{-1}$;

HRMS (ESI): [M+Na]$^+$ calculated for ([C$_9$H$_{15}$ClO$_3$Na]$^+$): 229.0602. found: 229.0593; The enantiomeric excess was determined by HPLC equipped with CHIRALPAK IA column ($^i$PrOH:hexane=1:10) (1 mL/min, the retention time of the major enantiomer=12.9 min, the retention time of the minor enantiomer=16.4 min) after 3,5-dinitrobenzoylation of the Wittig product.

(4R,5R,E)-ethyl 6-chloro-5-hydroxy-2,4-dimethyl-hex-2-enoate (Example 3-2)

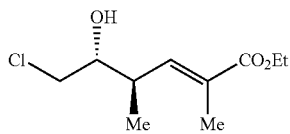 [SMILES: CCOC(=O)/C(C)=C/[C@@H](C)[C@@H](O)CCl]

as diastereomer mixture (anti:syn=5.65:1);

$^1$H NMR (CDCl$_3$, 400 MHz): δ1.10 (3H, d, J=6.8 Hz), 1.30 (3H, t, J=7.2 Hz), 1.88 (3H, d, J=1.2 Hz), 2.75-2.84 (1H, m), 3.52 (1H, dd, J=7.2, 11.2 Hz), 3.62 (1H, dd, J=3.6, 11.2 Hz), 3.73-3.77 (1H, m), 4.20 (2H, dq, J=1.2, 7.2 Hz), 6.69 (1H, dd, J=1.4, 10.2 Hz);

$^{13}$C NMR (CDCl$_3$, 100 MHz): δ13.1, 14.7, 16.5, 36.8, 48.3, 60.9, 74.7, 129.9, 141.4, 168.3;

IR (neat): $v_{max}$ 3484, 2979, 1708, 1648, 1369, 1280, 1139, 1094, 1005, 750, 405 cm$^{-1}$;

HRMS (ESI): [M+Na]$^+$ calculated for ([C$_{10}$H$_{17}$ClO$_3$Na]$^+$): 243.0758. found: 243.0754;

The enantiomeric excess was determined by HPLC equipped with CHIRALPAK AS-H column ($^i$PrOH:hexane=1:30) (1 mL/min, the retention time of the major enantiomer=11.2 min, the retention time of the minor enantiomer=13.4 min) after 3,5-dinitrobenzoylation of the Wittig product.

(4R,5R,E)-ethyl 6-chloro-4-ethyl-5-hydroxyhex-2-enoate (Example 3-3)

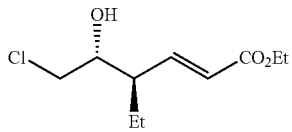

as diastereomer mixture (anti:syn=5.88:1);

$^1$H NMR (CDCl$_3$, 400 MHz): δ0.91 (3H, t, J=7.4 Hz), 1.30 (3H, t, J=3.2 Hz), 1.50-1.68 (2H, m), 2.18 (1H, d, J=4.4 Hz), 2.27-2.34 (1H, m), 3.49 (1H, dd, J=7.6, 11.2 Hz), 3.56 (1H, dd, J=4.0, 11.2 Hz), 3.83-3.87 (1H, m), 4.19 (2H, q, J=7.2 Hz), 5.88 (1H, dd, J=0.6, 15.8 Hz), 6.84 (1H, dd, J=9.8, 15.6 Hz);

$^{13}$C NMR (CDCl$_3$, 100 MHz): δ11.8, 14.0, 24.1, 47.8, 48.4, 60.3, 73.4, 124.5, 146.9, 166.3;

IR (neat): $v_{max}$ 3480, 2965, 1703, 1651, 1371, 1281, 1239, 1180, 1138, 1038, 991, 404 cm$^{-1}$;

HRMS (ESI): [M+Na]$^+$ calculated for ([C$_{10}$H$_{17}$ClO$_3$Na]$^+$): 243.0758. found: 243.0757;

The enantiomeric excess was determined by HPLC equipped with CHIRALPAK AD-H column ($^i$PrOH:hexane=1:50) (1 mL/min, the retention time of the major enantiomer=23.6 min, the retention time of the minor enantiomer=32.0 min) after 3,5-dinitrobenzoylation of the Wittig product.

(4R,5R,E)-ethyl 6-chloro-5-hydroxy-4-isopropylhex-2-enoate (Example 3-4)

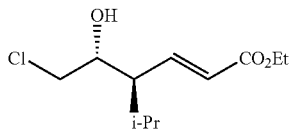 [SMILES: CCOC(=O)/C=C/[C@@H](C(C)C)[C@@H](O)CCl]

as diastereomer mixture (anti:syn=8.72:1);

$^1$H NMR (CDCl$_3$, 400 MHz): δ0.86 (3H, d, J=6.8 Hz), 0.96 (3H, d, J=6.4 Hz), 1.27 (3H, t, J=7.2 Hz), 1.87-1.96 (1H, m), 1.98-2.03 (1H, m), 2.06 (1H, d, J=3.6 Hz), 3.43 (1H, dd, J=7.8, 11.0 Hz), 3.48 (1H, dd, J=4.2, 11.0 Hz), 3.96-4.01 (1H, m), 4.17 (2H, q, J=7.2 Hz), 5.82 (1H, d, J=15.6 Hz), 6.87 (1H, dd, J=10.2, 15.8 Hz);

$^{13}$C NMR (CDCl$_3$, 100 MHz): δ14.4, 20.2, 20.9, 28.5, 49.1, 52.7, 60.7, 71.4, 125.1, 146.2, 166.0;

IR (neat): $v_{max}$ 3444, 2961, 2876, 1702, 1651, 1371, 1177, 1038, 995, 429, 412 cm$^{-1}$;

HRMS (ESI): [M+Na]$^+$ calculated for ([C$_{11}$H$_{19}$ClO$_3$Na]$^+$): 257.0915. found: 257.0926;

The enantiomeric excess was determined by HPLC equipped with CHIRALCEL OJ-H column ($^i$PrOH:hexane=1:30) (1 mL/min, the retention time of the minor enantiomer=23.0 min, the retention time of the major enantiomer=26.7 min) after 3,5-dinitrobenzoylation of the Wittig product.

(4R,5R,E)-ethyl 4-benzyl-6-chloro-5-hydroxyhex-2-enoate (Example 3-5)

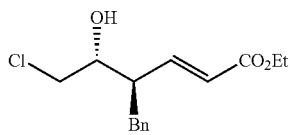 [SMILES: CCOC(=O)/C=C/[C@@H](CC)[C@@H](O)CCl]

as diastereomer mixture (anti:syn=6.90:1);
$^1$H NMR (CDCl$_3$, 400 MHz): δ1.28 (3H, t, J=7.2 Hz), 2.58-2.64 (1H, m), 2.78 (1H, dd, J=7.2, 13.6 Hz), 2.98 (1H, dd, J=3.8, 13.4 Hz), 4.17 (2H, dq, J=0.8, 6.0 Hz), 5.78 (1H, dd, J=6.0, 15.8 Hz), 6.96 (1H, dd, J=9.6, 15.6 Hz), 7.15-7.31 (5H, m);
$^{13}$C NMR (CDCl$_3$, 100 MHz): δ14.2, 37.3, 47.7, 48.9, 60.5, 71.8, 124.3, 126.4, 128.4, 129.3, 138.5, 146.2, 165.9;
IR (neat): $v_{max}$ 3421, 2927, 2356, 1699, 1653, 1496, 1456, 1371, 1280, 1161, 1033, 988, 701, 419 cm$^{-1}$;
HRMS (ESI): [M+Na]$^+$ calculated for ([C$_{15}$H$_{19}$ClO$_3$Na]$^+$): 305.0915. found: 305.0901;
The enantiomeric excess was determined by HPLC equipped with CHIRALPAK IA column ($^i$PrOH:hexane=1:30) (1 mL/min, the retention time of the major enantiomer=27.3 min, the retention time of the minor enantiomer=40.6 min) after 3,5-dinitrobenzoylation of the Wittig product.

(R,2E,7Z)-ethyl 4-((R)-2-chloro-1-hydroxyethyl) dec-2,7-dienoate (Example 3-6)

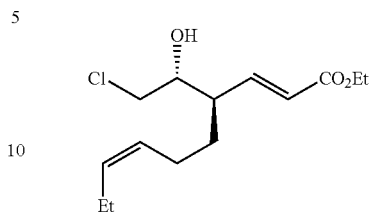

as diastereomer mixture (anti:syn=5.88:1);
$^1$H NMR (CDCl$_3$, 400 MHz): δ0.95 (3H, t, J=7.4 Hz), 1.30 (3H, t, J=7.0 Hz), 1.97-2.06 (4H, m), 2.20 (1H, d, J=3.6 Hz), 2.40-2.47 (1H, m), 3.49 (1H, dd, J=8.0, 11.2 Hz), 3.55 (1H, dd, J=4.0, 11.2 Hz), 3.81-3.85 (1H, m), 4.20 (2H, q, J=7.2 Hz), 5.23-5.43 (2H, m), 5.88 (1H, dd, J=0.6, 15.8 Hz), 6.85 (1H, dd, J=9.8, 15.8 Hz);
$^{13}$C NMR (CDCl$_3$, 100 MHz): δ14.7, 20.8, 24.8, 45.3, 48.7, 60.7, 124.3, 127.9, 133.1, 147.1, 166.3;
IR (neat): $v_{max}$ 3464, 2964, 1710, 1702, 1652, 1372, 1280, 1162, 1036, 991, 727, 420 cm$^{-1}$;
HRMS (ESI): [M+Na]$^+$ calculated for ([C$_{14}$H$_{23}$ClO$_3$Na]$^+$): 297.1228. found: 297.1235;
The enantiomeric excess was determined by HPLC equipped with CHIRALPAK AD-H column ($^i$PrOH:hexane=1:100) (1 mL/min, the retention time of the major enantiomer=51.7 min, the retention time of the minor enantiomer=64.3 min) after 3,5-dinitrobenzoylation of the Wittig product.

TABLE 3

| Example | Product | X (mmol) | Y (mmol) | Time (hr) | Yield (%) | anti:syn | ee (%) |
|---|---|---|---|---|---|---|---|
| 3-1 | -CH(Me)-CH=CH-CO2Et) | 0.5 | 1.0 | 33 | 75 | 4.2:1 | 95 |
| 3-2 | -CH(Me)-C(Me)=CH-CO2Et) | 0.5 | 1.0 | 38 | 74 | 5.6:1 | 94 |
| 3-3 | -CH(Et)-CH=CH-CO2Et) | 0.5 | 1.0 | 36 | 66 | 5.9:1 | 99 |
| 3-4 | -CH(i-Pr)-CH=CH-CO2Et) | 0.5 | 1.0 | 90 | 44 | 8.7:1 | 98 |
| 3-5 | -CH(Bn)-CH=CH-CO2Et) | 0.75 | 0.5 | 82 | 70 | 6.9:1 | 98 |

TABLE 3-continued

| Example | Product | X (mmol) | Y (mmol) | Time (hr) | Yield (%) | anti:syn | ee (%) |
|---|---|---|---|---|---|---|---|
| 3-6 | 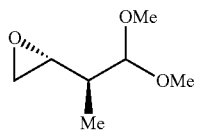 | 0.75 | 0.5 | 46 | 74 | 5.9:1 | 96 |

Examples 4-1–4-5

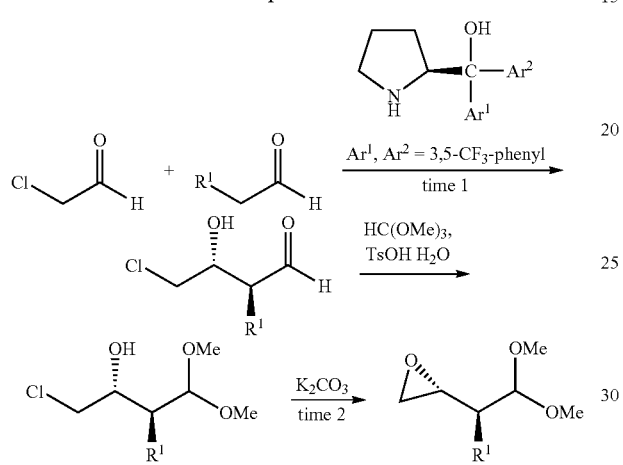

To a 40% aqueous chloroacetaldehyde solution (the amount (X) shown in Table 4) were added (S)-2-[bis(3,5-bis-trifluoromethylphenyl)hydroxymethyl]pyrrolidine (0.05 mmol, except that 0.075 mmol was used in Examples 4-3 and 4-5), THF (0.5 mL) and aldehyde compound (1) (the amount (Y) shown in Table 4). The reaction mixture was stirred at 23° C. for the time shown in Table 4 (time-1), trimethyl orthoformate (492 μL, 4.5 mmol) and p-toluenesulfonic acid monohydrate (19.0 mg, 0.1 mmol) were added thereto, and the mixture was stirred at 23° C. for 1 hr. Then, $K_2CO_3$ (173 mg, 1.25 mmol) and MeOH (0.5 mL) were added thereto at 0° C. The reaction mixture was stirred at 65° C. for the time shown in Table 4 (time-2), and cooled water was added thereto at 23° C. The organic materials were extracted with chloroform (threetimes), and the extract was dried over anhydrous $MgSO_4$, filtered, and concentrated under reduced pressure. The residue was purified by column chromatography (ethyl acetate:hexane=1:6) to give epoxy compound (6) ($R^2$=methyl). The yield, syn/anti ratio and enantiomeric excess are shown in Table 4. The yield was calculated as a yield over three steps. The syn/anti ratio was determined by $^1$H-NMR spectrum. The enantiomeric excess was determined by HPLC equipped with chiral column.

(R)-2-((S)-1,1-dimethoxypropan-2-yl)oxirane (Example 4-1)

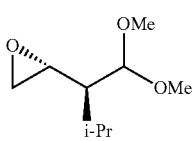 [SMILES: COC(OC)[C@@H](C(C)C)[C@@H]1CO1]

as diastereomer mixture (anti:syn=4.76:1);

$^1$H NMR (CDCl$_3$, 400 MHz): δ0.88 (3H, dd, J=3.0, 7.0 Hz), 1.62-1.67 (1H, m), 2.44 (1H, dd, J=2.8, 4.8 Hz), 2.67 (1H, dt, J=4.0, 4.8 Hz), 2.86 (1H, ddd, J=2.8, 3.6, 7.0 Hz), 3.35 (3H, d, J=3.2 Hz), 3.37 (3H, d, J=3.2 Hz), 4.25 (1H, dd, J=3.2, 5.2 Hz);

$^{13}$C NMR (CDCl$_3$, 100 MHz): δ10.0, 39.5, 44.9, 53.3, 54.6, 54.7, 107.1;

IR (neat): ν$_{max}$ 2929, 1733, 1698, 1558, 1541, 1507, 1457, 1374, 1281, 1175, 1138, 901, 682, 668, 458, 436, 422, 411 cm$^{-1}$;

HRMS (ESI): [M+Na]$^+$ calculated for ([C$_7$H$_{14}$O$_3$Na]): 169.0835. found: 169.0837.

(R)-2-((S)-1,1-dimethoxybutan-2-yl)oxirane (Example 4-2)

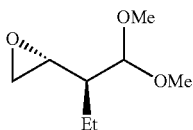 [SMILES: CC[C@H](C(OC)OC)[C@@H]1CO1]

as diastereomer mixture (anti:syn=6.67:1);

$^1$H NMR (CDCl$_3$, 400 MHz): δ0.95 (3H, t, J=7.6 Hz), 1.32-1.47 (2H, m), 1.60-1.66 (1H, m), 2.53 (1H, q, J=2.4 Hz), 2.78 (1H, dd, J=4.0, 4.8 Hz), 2.87 (1H, ddd, J=3.2, 4.0, 7.8 Hz), 3.41 (3H, s), 3.44 (3H, s), 4.38 (1H, d, J=4.4 Hz);

$^{13}$C NMR (CDCl$_3$, 100 MHz): δ12.0, 18.8, 46.4, 46.7, 52.3, 55.2, 55.6, 106.6;

IR (neat): ν2965, 1466, 1374, 1281, 1177, 1141, 1073, 968, 844, 683, 419, 402 cm$^{-1}$;

HRMS (ESI): [M+Na]$^+$ calculated for ([C$_8$H$_{16}$O$_3$Na]): 183.0992. found: 183.0987.

(R)-2-((S)-1,1-dimethoxy-3-methylbutan-2-yl)oxirane (Example 4-3)

as diastereomer mixture (anti:syn=8.33:1);

$^1$H NMR (CDCl$_3$, 400 MHz): δ0.96 (6H, dt, J=1.2, 7.0 Hz), 1.17-1.22 (2H, m), 1.94-2.04 (1H, m), 2.51 (1H, ddd, J=1.6, 2.4, 6.0 Hz), 2.75-2.77 (1H, m), 2.86-2.89 (1H, m), 3.62 (3H, s), 3.65 (3H, s), 4.44 (1H, dd, J=1.4, 5.4 Hz);

$^{13}$C NMR (CDCl$_3$, 100 MHz): δ19.3, 22.0, 26.6, 46.3, 49.8, 50.6, 54.5, 54.6, 106.2;

IR (neat): ν2960, 1464, 1373, 1281, 1176, 1138, 1074, 682, 419, 410 cm$^{-1}$;

HRMS (ESI): [M+Na]$^+$ calculated for ([C$_9$H$_{18}$O$_3$Na]): 197.1148. found: 197.1147.

(R)-2-((S)-1,1-dimethoxy-3-phenylpropan-2-yl)oxirane (Example 4-4)

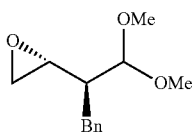 [SMILES: COC(OC)[C@@H](Cc1ccccc1)[C@@H]1CO1]

as diastereomer mixture (anti:syn=8.3:1);

$^1$H NMR (CDCl$_3$, 400 MHz): δ1.67-1.72 (1H, m), 2.00 (1H, dd, J=2.8, 4.8 Hz), 2.54 (1H, dd, J=4.4, 4.8 Hz), 2.62 (1H, dd, J=10.0, 14.0 Hz), 2.88-2.98 (2H, m), 3.45 (3H, s), 3.48 (3H, s), 4.40 (1H, dd, J=4.4 Hz), 7.15-7.30 (5H, m);

$^{13}$C NMR (CDCl$_3$, 100 MHz): δ32.0, 46.4, 47.6, 51.9, 55.3, 55.9, 106.6, 126.1, 128.4, 129.1, 140.6;

IR (neat): ν2832, 1496, 1455, 1361, 1281, 1200, 1136, 1073, 971, 881, 838, 745, 702, 520, 457, 438, 417, 405 cm$^{-1}$;

HRMS (ESI): [M+Na]$^+$ calculated for ([C$_{13}$H$_{18}$O$_3$Na]): 245.1148. found: 245.1143;

The enantiomeric excess was determined by HPLC equipped with CHIRALPAK AD-H column ($^i$PrOH:hexane=1:200) (1 mL/min, the retention time of the major enantiomer=8.1 min, the retention time of the minor enantiomer=12.0 min).

(R)-2-((S,Z)-1,1-dimethoxyoct-5-en-2-yl)oxirane (Example 4-5)

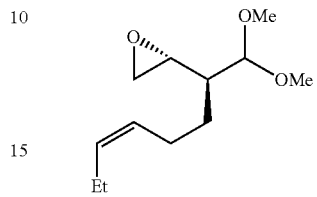

as diastereomer mixture (anti:syn=5.3:1);

$^1$H NMR (CDCl$_3$, 400 MHz): δ0.96 (3H, t, J=7.6 Hz), 1.37-1.67 (2H, m), 2.01-2.20 (5H, m), 2.52 (1H, dd, J=2.8, 5.2 Hz), 2.78-2.80 (1H, m), 3.41 (3H, s), 3.45 (3H, s), 4.38 (1H, d, J=4.4 Hz), 5.29-5.35 (2H, m);

$^{13}$C NMR (CDCl$_3$, 100 MHz): δ14.3, 20.6, 25.0, 26.0, 44.4, 46.5, 52.3, 55.2, 55.7, 128.8, 132.2;

IR (neat): ν3003, 2963, 2931, 2832, 1733, 1457, 1373, 1281, 1188, 1140, 1075, 968, 845, 805, 668, 503, 472, 419, 410, 401 cm$^{-1}$;

HRMS (ESI): [M+Na]$^+$ calculated for ([C$_{12}$H$_{22}$O$_3$Na]): 237.1461. found: 237.1469.

TABLE 4

| Example | Product | X (mmol) | Y (mmol) | Time-1 (hr) | Time-2 (hr) | Yield (%) | anti:syn | ee (%) |
|---|---|---|---|---|---|---|---|---|
| 4-1 | (epoxide with OMe, OMe, Me) | 0.5 | 1.0 | 33 | 5 | 82 | 4.8:1 | 95 |
| 4-2 | (epoxide with OMe, OMe, Et) | 0.5 | 1.0 | 38 | 8 | 80 | 6.7:1 | 97 |
| 4-3 | (epoxide with OMe, OMe, i-Pr) | 0.5 | 1.0 | 90 | 10 | 78 | 8.3:1 | 97 |
| 4-4 | (epoxide with OMe, OMe, Bn) | 0.75 | 0.5 | 82 | 1.5 | 63 | 8.3:1 | 99 |
| 4-5 | (epoxide with OMe, OMe, CH$_2$CH=CHEt) | 0.75 | 0.5 | 46 | 5 | 82 | 5.3:1 | 98 |

Examples 5-1-5-6

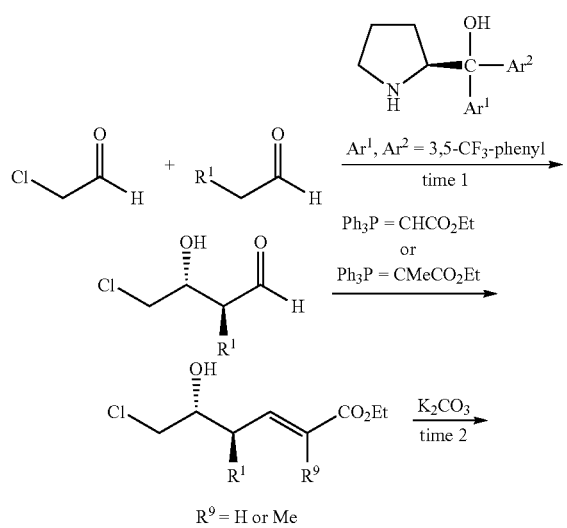

$R^9$ = H or Me

To a 40% aqueous chloroacetaldehyde solution (the amount (X) shown in Table 5) were added (S)-2-[bis(3,5-bis-trifluoromethylphenyl)hydroxymethyl]pyrrolidine (0.05 mmol, except that 0.075 mmol was used in Examples 5-4 and 5-6), THF (0.5 mL) and aldehyde compound (1) (the amount (Y) shown in Table 5). The reaction mixture was stirred at 23° C. for the time shown in Table 5 (time-1), the Wittig reagent (435 mg, 1.25 mmol) was added thereto, and the mixture was stirred at 23° C. for 1 hr. Then, $K_2CO_3$ (138 mg, 1.00 mmol) and EtOH (0.5 mL) was added thereto at 23° C., and the reaction mixture was stirred at 65° C. for the time shown in Table 5 (time-2). The reaction was quenched by through silica gel pad, and concentrated under reduced pressure. The residue was purified by preparative thin layer chromatography (ethyl acetate:hexane=1:5) to give epoxy compound (7) ($R^9$=a hydrogen atom or methyl, and $R^{10}$=ethyl). The yield, syn/anti ratio and enantiomeric excess are shown in Table 5. The yield was calculated as a yield over three steps. The syn/anti ratio was determined by $^1$H-NMR spectrum. The enantiomeric excess was determined by HPLC equipped with chiral column.

(R,E)-ethyl 4-((R)-oxiran-2-yl)pent-2-enoate (Example 5-1)

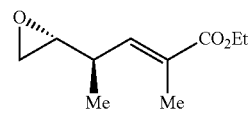

as diastereomer mixture (anti:syn=7.85:1);
$^1$H NMR (CDCl$_3$, 400 MHz): δ1.13 (3H, d, J=7.2 Hz), 1.29 (3H, t, J=7.2 Hz), 2.23-2.34 (1H, m), 2.55 (1H, dd, J=3.2, 4.8 Hz), 2.76-2.78 (1H, m), 2.89 (1H, ddd, J=3.2, 4.0, 6.8 Hz), 4.20 (2H, q, J=7.2 Hz), 5.92 (1H, dd, J=1.5, 16.0 Hz), 6.93 (1H, dd, J=7.0, 16.0 Hz);
$^{13}$C NMR (CDCl$_3$, 100 MHz): δ14.2, 15.3, 38.5, 45.7, 54.8, 60.4, 121.9, 148.8, 166.5;
IR (neat): $v_{max}$ 2979, 1719, 1655, 1368, 1269, 1184, 1037, 984, 894, 428, 405 cm$^{-1}$;
HRMS (ESI): [M+Na]$^+$ calculated for ([C$_9$H$_{14}$O$_3$Na]$^+$): 193.0835. found: 193.0834.

(R,E)-ethyl 2-methyl-4-((R)-oxiran-2-yl)pent-2-enoate (Example 5-2)

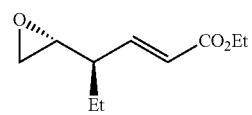

as diastereomer mixture (anti:syn=5.04:1);
$^1$H NMR (CDCl$_3$, 400 MHz): δ1.10 (3H, d, J=6.8 Hz), 1.30 (3H, t, J=7.0 Hz), 1.86 (3H, d, J=1.2), 2.54 (1H, dd, J=2.8, 4.8 Hz), 2.52-2.60 (1H, m), 2.74 (1H, dd, J=4.0, 4.8 Hz), 2.90-2.93 (1H, m), 4.17-4.22 (2H, m), 6.59 (1H, dd, J=1.4, 9.8 Hz);
$^{13}$C NMR (CDCl$_3$, 100 MHz): δ13.0, 14.6, 16.0, 35.5, 45.5, 55.5, 60.6, 129.3, 141.6, 168.3;
IR (neat): $v_{max}$ 2979, 2932, 2360, 1712, 1652, 1457, 1367, 1295, 1243, 1175, 1099, 896, 749 cm$^{-1}$;
HRMS (ESI): [M+Na]$^+$ calculated for ([C$_{10}$H$_{16}$O$_3$Na]$^+$): 207.0992. found: 207.0984.

(R,E)-ethyl 4-((R)-oxiran-2-yl)hex-2-enoate (Example 5-3)

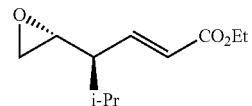 [SMILES: CCOC(=O)/C=C/[C@@H](C(C)C)[C@@H]1CO1]

as diastereomer mixture (anti:syn=4.60:1);
$^1$H NMR (CDCl$_3$, 400 MHz): δ0.95 (3H, t, J=7.6 Hz), 1.29 (3H, t, J=7.2 Hz), 1.46-1.65 (4H, m), 2.01 (1H, quin., J=7.2 Hz), 2.55 (1H, dd, J=2.8, 4.8), 2.80 (1H, t, J=4.4 Hz), 2.91 (1H, ddd, J=2.8, 3.8, 6.8 Hz), 4.19 (2H, q, J=7.0 Hz), 5.92 (1H, dd, J=0.8, 15.6 Hz), 6.83 (1H, dd, J=8.4, 16.0 Hz);
$^{13}$C NMR (CDCl$_3$, 100 MHz): δ11.6, 14.2, 23.9, 46.1, 46.2, 54.0, 60.3, 123.0, 147.8, 166.2;
IR (neat): $v_{max}$ 2970, 2361, 1719, 1653, 1368, 1237, 1182, 1038, 984, 668, 422, 413 cm$^{-1}$;
HRMS (ESI): [M+Na]$^+$ calculated for ([C$_{10}$H$_{16}$O$_3$Na]$^+$): 207.0992. found: 207.0992.

(R,E)-ethyl 5-methyl-4-((R)-oxiran-2-yl)hex-2-enoate (Example 5-4)

as diastereomer mixture (anti:syn=6.25:1);

¹H NMR (CDCl₃, 400 MHz): δ0.96 (3H, d, J=6.8 Hz), 1.01 (3H, d, J=6.8 Hz), 1.29 (3H, t, J=7.2 Hz), 1.76-1.82 (1H, m), 1.85-1.94 (1H, m), 2.54 (1H, dd, J=2.8, 4.8 Hz), 2.83 (1H, dd, J=4.0, 4.8 Hz), 2.96 (1H, ddd, J=2.8, 4.0, 6.8 Hz), 4.19 (2H, q, J=7.2 Hz), 5.90 (1H, dd, J=0.8, 15.6 Hz), 6.86 (1H, dd, J=8.8, 15.6 Hz);
¹³C NMR (CDCl₃, 100 MHz): δ14.2, 20.3, 20.5, 30.6, 46.9, 51.7, 53.1, 60.3, 109.6, 123.8, 146.8;
IR (neat): ν$_{max}$ 2963, 2359, 1720, 1652, 1470, 1369, 1280, 1180, 1040, 984, 806, 567, 443, 422 cm⁻¹;
HRMS (ESI): [M+Na]⁺ calculated for ([C₁₁H₁₈O₃Na]⁺): 221.1148. found: 221.1148.

(R,E)-ethyl 4-((R)-oxiran-2-yl)-5-phenylpent-2-enoate (Example 5-5)

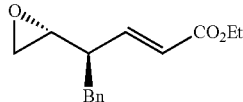 [SMILES: CCOC(=O)/C=C/[C@@H](Cc1ccccc1)[C@@H]1CO1]

as diastereomer mixture (anti:syn=9.09:1);
¹H NMR (CDCl₃, 400 MHz): δ1.28 (3H, d, J=6.8 Hz), 2.32 (1H, q, J=2.4 Hz), 2.36-2.44 (1H, m), 2.67 (1H, dd, J=4.2, 4.6 Hz), 2.84 (1H, dd, J=4.6, 7.4 Hz), 2.94 (1H, ddd, J=2.8, 4.0, 6.4 Hz), 4.19 (2H, q, J=7.2 Hz), 5.89 (1H, dd, J=1.2, 15.6 Hz), 6.90 (1H, q, J=8.0 Hz);
¹³C NMR (CDCl₃, 100 MHz): δ14.2, 37.6, 41.4, 46.4, 53.6, 60.4, 123.2, 126.6, 128.5, 129.0, 138.3, 147.0, 166.1;
IR (neat): ν$_{max}$ 1720, 1651, 1454, 1368, 1269, 1193, 982, 984, 701, 431, 405 cm⁻¹;

HRMS (ESI): [M+Na]⁺ calculated for ([C₁₅H₁₈O₃Na]): 269.1148. found: 267.1139;
The enantiomeric excess was determined by HPLC equipped with CHIRALPAK IC column (ⁱPrOH:hexane=1:30) (1 mL/min, the retention time of the major enantiomer=25.3 min, the retention time of the minor enantiomer-27.1 min).

(R,2E,7Z)-ethyl 4-((R)-oxiran-2-yl)dec-2,7-dienoate (Example 5-6)

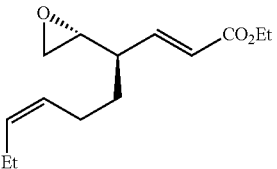 [SMILES: CC/C=C\CC[C@H](/C=C/C(=O)OCC)[C@@H]1CO1]

as diastereomer mixture (anti:syn=4.80:1);
¹H NMR (CDCl₃, 400 MHz): δ0.96 (3H, t, J=7.6 Hz), 1.29 (3H, t, J=7.2 Hz), 1.50-1.67 (2H, m), 1.98-2.19 (5H, m), 2.55 (1H, dd, J=2.8, 4.8 Hz), 2.79 (1H, dd, J=4.0, 5.2 Hz), 2.91 (1H, ddd, J=2.8, 4.0, 6.8), 4.20 (2H, q, J=7.2 Hz), 5.22-5.43 (2H, m), 5.92 (1H, dd, J=1.2, 16.0 Hz), 6.83 (1H, dd, J=8.4, 16.0 Hz);
¹³C NMR (CDCl₃, 100 MHz): δ14.4, 20.7, 24.6, 31.1, 44.1, 46.4, 53.9, 60.1, 123.3, 127.9, 132.8, 147.7, 166.2;
IR (neat): ν$_{max}$ 2964, 1720, 1653, 1464, 1368, 1268, 1191, 1037, 983, 720, 437, 418 cm⁻¹;
HRMS (ESI): [M+Na]⁺ calculated for ([C₁₄H₂₂O₃Na]⁺): 261.1461. found: 267.1457.

TABLE 5

| Example | Product | X (mmol) | Y (mmol) | Time-1 (hr) | Time-2 (hr) | Yield (%) | anti:syn | ee (%) |
|---|---|---|---|---|---|---|---|---|
| 5-1 | (Me) | 0.5 | 1.0 | 33 | 6 | 75 | 4.8:1 | 95 |
| 5-2 | (Me, Me) | 0.5 | 1.0 | 38 | 7 | 79 | 5.0:1 | 94 |
| 5-3 | (Et) | 0.5 | 1.0 | 36 | 8.5 | 72 | 4.6:1 | 99 |
| 5-4 | (i-Pr) | 0.5 | 1.0 | 90 | 12 | 61 | 6.3:1 | 98 |
| 5-5 | (Bn) | 0.75 | 0.5 | 82 | 3 | 70 | 9.1:1 | 98 |

TABLE 5-continued

| Example | Product | X (mmol) | Y (mmol) | Time-1 (hr) | Time-2 (hr) | Yield (%) | anti:syn | ee (%) |
|---|---|---|---|---|---|---|---|---|
| 5-6 | 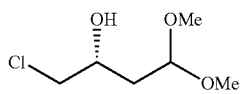 | 0.75 | 0.5 | 46 | 6 | 78 | 4.8:1 | 96 |

Example 6 (R)-1-chloro-4,4-dimethoxybutan-2-ol

To a 40% aqueous chloroacetaldehyde solution (19.6 g, 0.1 mol) was added $CHCl_3$ (18.8 ml), and the mixture was heated under reflux using Dean-Stark at 65° C. for 48 hr. The water (about 10 mL) was removed, and the $CHCl_3$ was evaporated under reduced pressure. To the residue (39.3 mg, 0.5 mmol) were added THF (0.5 mL), acetaldehyde (aldehyde compound (1), 1.5 mmol) and a pyrrolidine compound (0.05 mmol, 10 mol % relative to acetaldehyde) as a catalyst. The reaction mixture was stirred at 23° C. for 24 hr, trimethyl orthoformate (492 μL, 4.5 mmol) and p-toluenesulfonic acid monohydrate (19.0 mg, 0.1 mmol) were added thereto, and the mixture was stirred at 23° C. for 1 hr. The reaction was quenched by the addition of saturated aqueous sodium hydrogen carbonate solution. The organic materials were extracted with chloroform (threetimes), and the extract was dried over anhydrous $MgSO_4$, filtered, and concentrated under reduced pressure. The residue was purified by column chromatography (ethyl acetate:hexane=1:5) to give acetal compound (3) ($R^1$=a hydrogen atom, and $R^2$=methyl). The yield was 52%, and the enantiomeric excess was 78% ee. The yield was calculated as a yield over two steps. The enantiomeric excess was determined by HPLC equipped with chiral column after convertion to the corresponding 3,5-dinitrobenzoate.

$^1$H NMR ($CDCl_3$, 400 MHz): δ1.86-1.90 (2H, m), 3.05 (1H, br-d, J=3.2 Hz), 3.38 (3H, s), 3.38 (3H, s), 3.53-3.57 (2H, m), 4.00-4.02 (1H, m), 4.61 (1H, t, J=5.6 Hz);

$^{13}$C NMR ($CDCl_3$, 100 MHz): δ36.8, 49.4, 53.5, 53.9, 68.4, 103.3;

IR (neat): $v_{max}$ 3450, 2963, 2835, 1727, 1648, 1447, 1374, 1281, 1189, 1128, 1057, 962, 902, 822, 745, 683, 409 $cm^{-1}$;

HRMS (ESI): [M+Na]$^+$ calculated for ([$C_6H_{13}ClO_3Na$]$^+$): 191.0445. found: 191.0441;

[α]$_D$22-9.72° (c=1.80, $CHCl_3$);

The enantiomeric excess was determined by HPLC equipped with CHIRALPAK AD-H column ($^i$PrOH:hexane=1:30) (1 mL/min, the retention time of the major enantiomer=17.4 min, the retention time of the minor enantiomer=12.9 min) after 3,5-dinitrobenzoylation of the acetalization product.

INDUSTRIAL APPLICABILITY

According to the production method of the present invention, optically active 4-chloro-3-hydroxybutanal compound (2) can be produced.

The invention claimed is:

1. A method of producing an optically active compound represented by the formula (2):

wherein
$R^1$ is a $C_1$-$C_{20}$ hydrocarbon group optionally having substituent(s) selected from the following Group G1 or a hydrogen atom, and
the carbon atom marked with ** is an asymmetric carbon atom,
which comprises a step of reacting chloroacetaldehyde with a compound represented by the formula (1):

$$R^1—CH_2CHO \quad (1)$$

wherein
$R^1$ is as defined above,
in the presence of an optically active compound represented by the formula (5):

wherein
$Ar^1$ and $Ar^2$ are each independently a phenyl group optionally having substituent(s) selected from the following Group G2, a $C_1$-$C_{12}$ chain hydrocarbon group, a $C_3$-$C_{12}$ alicyclic hydrocarbon group or a hydrogen atom,
$R^5$ is a hydrogen atom, a fluorine atom, a hydroxyl group, a $C_1$-$C_{12}$ alkoxy group, a $C_1$-$C_{12}$ fluorinated alkyloxy group or a group represented by —OSi$R^6R^7R^8$ wherein $R^6$, $R^7$ and $R^8$ are each independently a $C_1$-$C_8$ alkyl group or a $C_6$-$C_{20}$ aryl group, and
the carbon atom marked with * is an asymmetric carbon atom;
<Group G1>: a group consisting of a $C_6$-$C_{20}$ aryl group optionally having substituent(s) selected from Group G2, an aromatic heterocyclic group optionally having substituent(s) selected from Group G2, a $C_1$-$C_{12}$ alkoxy group, a $C_1$-$C_{12}$ alkoxy group having $C_6$-$C_{20}$ aryl group(s) optionally having substituent(s) selected from Group G2, a halogen atom, an oxo group and a tri-$C_1$-$C_{12}$ alkylsilyl group;

<Group G2>: a group consisting of a $C_1$-$C_{12}$ alkyl group, a $C_1$-$C_{12}$ alkoxy group, a $C_2$-$C_{13}$ alkoxycarbonyl group, a $C_1$-$C_{12}$ fluorinated alkyl group, a $C_2$-$C_{13}$ acyl group, a nitro group, a cyano group, a protected amino group and a halogen atom.

2. The method of claim 1, wherein the reaction is carried out in a solvent containing an organic solvent.

3. The method of claim 1, wherein $R^1$ is not a hydrogen atom, and the reaction is carried out in a mixed solvent of water and an organic solvent selected from an alcohol solvent, an ether solvent, a nitrile solvent and an aprotic polar solvent.

4. The method of claim 1, wherein $R^5$ is a hydroxyl group.

5. The method of claim 1, wherein $R^5$ is a hydroxyl group, and $Ar^1$ and $Ar^2$ are each independently a phenyl group optionally having $C_1$-$C_{12}$ fluorinated alkyl group(s).

6. The method of claim 1, wherein $R^5$ is a hydroxyl group, and $Ar^1$ and $Ar^2$ are both 3,5-bis(trifluoromethyl)phenyl groups.

7. A method of producing an optically active compound represented by the formula (3):

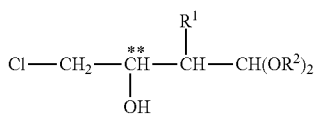

(3)

wherein
$R^1$ and ** are as defined in claim 1, and
$R^2$ is a $C_1$-$C_{10}$ alkyl group, and two of $R^2$ in combination form a $C_2$-$C_{10}$ alkanediyl group optionally having substituent(s) selected from the following Group G1,
which comprises
a step of producing an optically active compound represented by the formula (2):

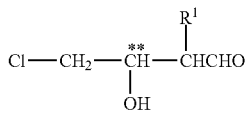

(2)

wherein $R^1$ and ** are as defined in claim 1,
according to the method of claim 1; and
a step of subjecting the optically active compound represented by the formula (2) obtained the above-mentioned step to acetalization;

<Group G1>: a group consisting of a $C_6$-$C_{20}$ aryl group optionally having substituent(s) selected from Group G2, an aromatic heterocyclic group optionally having substituent(s) selected from Group G2, a $C_1$-$C_{12}$ alkoxy group, a $C_1$-$C_{12}$ alkoxy group having $C_6$-$C_{20}$ aryl group(s) optionally having substituent(s) selected from Group G2, a halogen atom, an oxo group and a tri-$C_1$-$C_{12}$ alkylsilyl group;

<Group G2>: a group consisting of a $C_1$-$C_{12}$ alkyl group, a $C_1$-$C_{12}$ alkoxy group, a $C_2$-$C_{13}$ alkoxycarbonyl group, a $C_1$-$C_{12}$ fluorinated alkyl group, a $C_2$-$C_{13}$ acyl group, a nitro group, a cyano group, a protected amino group and a halogen atom.

8. A method of producing an optically active compound represented by the formula (6):

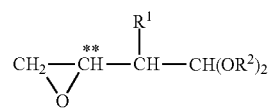

(6)

wherein
$R^1$ and ** are as defined in claim 1, and
$R^2$ is a $C_1$-$C_{10}$ alkyl group, and two of $R^2$ in combination form a $C_2$-$C_{10}$ alkanediyl group optionally having substituent(s) selected from the following Group G1,
which comprises
a step of producing an optically active compound represented by the formula (2):

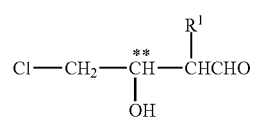

(2)

wherein $R^1$ and ** are as defined in claim 1,
according to the method of claim 1;
a step of subjecting the optically active compound represented by the formula (2) obtained the above-mentioned step to acetalization; and
a step of reacting the optically active compound represented by the formula (3):

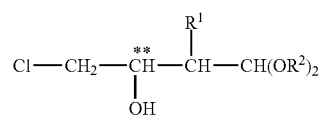

(3)

wherein
$R^1$ and ** are as defined in claim 1, and
$R^2$ is as defined above,
which is obtained the above-mentioned step, with a base;

<Group G1>: a group consisting of a $C_6$-$C_{20}$ aryl group optionally having substituent(s) selected from Group G2, an aromatic heterocyclic group optionally having substituent(s) selected from Group G2, a $C_1$-$C_{12}$ alkoxy group, a $C_1$-$C_{12}$ alkoxy group having $C_6$-$C_{20}$ aryl group(s) optionally having substituent(s) selected from Group G2, a halogen atom, an oxo group and a tri-$C_1$-$C_{12}$ alkylsilyl group;

<Group G2>: a group consisting of a $C_1$-$C_{12}$ alkyl group, a $C_1$-$C_{12}$ alkoxy group, a $C_2$-$C_{13}$ alkoxycarbonyl group, a $C_1$-$C_{12}$ fluorinated alkyl group, a $C_2$-$C_{13}$ acyl group, a nitro group, a cyano group, a protected amino group and a halogen atom.

9. A method of producing an optically active compound represented by the formula (4):

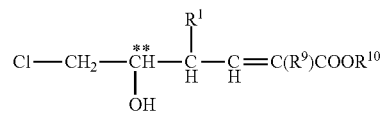

(4)

wherein
$R^1$ and ** are as defined in claim 1,
$R^9$ is a hydrogen atom or a $C_1$-$C_8$ alkyl group, and
$R^{10}$ is a $C_1$-$C_8$ alkyl group, which comprises a step of producing an optically active compound represented by the formula (2):

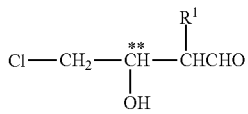

(2)

wherein $R^1$ and  are as defined in claim 1, according to the method of claim 1**; and a step of reacting the optically active compound represented by the formula (2) obtained the above-mentioned step with $Ph_3P=C(R^9)CO_2R^{10}$ wherein Ph is a phenyl group, and $R^9$ and $R^{10}$ are as defined above.

10. A method of producing an optically active compound represented by the formula (7):

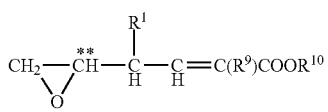

(7)

wherein $R^1$ and  are as defined in claim 1**, $R^9$ is a hydrogen atom or a $C_1$-$C_8$ alkyl group, and $R^{10}$ is a $C_1$-$C_8$ alkyl group, which comprises a step of producing an optically active compound represented by the formula (2):

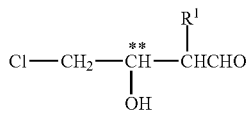

(2)

wherein $R^1$ and  are as defined in claim 1, according to the method of claim 1**;

a step of reacting the optically active compound represented by the formula (2) obtained the above-mentioned step with $Ph_3P=C(R^9)CO_2R^{10}$ wherein Ph is a phenyl group, and $R^9$ and $R^{10}$ are as defined above; and a step of reacting the optically active compound represented by the formula (4):

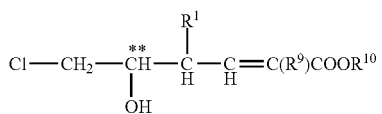

(4)

wherein $R^1$ and  are as defined in claim 1**, and $R^9$ and $R^{10}$ are as defined above, which is obtained the above-mentioned step, with a base.

* * * * *

UNITED STATES PATENT AND TRADEMARK OFFICE
CERTIFICATE OF CORRECTION

PATENT NO. : 8,742,176 B2
APPLICATION NO. : 13/880640
DATED : June 3, 2014
INVENTOR(S) : Yujiro Hayashi It is certified that error appears in the above-identified patent and that said Letters Patent is hereby corrected as shown below:

IN THE CLAIMS:

Claim 1, column 40, line 41, delete "(6)" and insert -- (5) --.

Claim 3, column 41, line 8, delete "$R^{l}$" and insert -- $R^1$ --.

Signed and Sealed this
Ninth Day of December, 2014

Michelle K. Lee
*Deputy Director of the United States Patent and Trademark Office*